(12) United States Patent
Chiu et al.

(10) Patent No.: US 10,590,470 B2
(45) Date of Patent: *Mar. 17, 2020

(54) METHODS AND SYSTEMS FOR PERFORMING DIGITAL MEASUREMENTS

(71) Applicant: University of Washington Through Its Center for Commercialization, Seattle, WA (US)

(72) Inventors: Daniel T. Chiu, Seattle, WA (US); Bryant S. Fujimoto, Seattle, WA (US); Alexander R. Gansen, Seattle, WA (US); Gloria S. Yen, Seattle, WA (US); Robert M. Lorenz, Walnut Creek, CA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/962,944

(22) Filed: Apr. 25, 2018

(65) Prior Publication Data

US 2018/0251827 A1   Sep. 6, 2018

Related U.S. Application Data

(60) Continuation of application No. 15/230,162, filed on Aug. 5, 2016, now Pat. No. 10,000,797, which is a division of application No. 13/980,457, filed as application No. PCT/US2012/022081 on Jan. 20, 2012, now Pat. No. 9,428,793.

(60) Provisional application No. 61/434,670, filed on Jan. 20, 2011.

(51) Int. Cl.
*C12Q 1/68* (2018.01)
*C12Q 1/6851* (2018.01)
*C12Q 1/6806* (2018.01)

(52) U.S. Cl.
CPC ......... *C12Q 1/6851* (2013.01); *C12Q 1/6806* (2013.01)

(58) Field of Classification Search
CPC ............ C12Q 1/6851; C12Q 2527/146; C12Q 2545/114; C12Q 2563/159
See application file for complete search history.

(56) References Cited

U.S. PATENT DOCUMENTS

| | | | |
|---|---|---|---|
| 9,428,793 | B2 | 8/2016 | Chiu et al. |
| 10,000,797 | B2 | 6/2018 | Chiu et al. |
| 2007/0298515 | A1 | 12/2007 | Diamond et al. |
| 2009/0203063 | A1 | 8/2009 | Wheeler et al. |
| 2010/0097590 | A1 | 4/2010 | Schumaker |
| 2010/0105025 | A1 | 4/2010 | Engelhard |
| 2010/0136544 | A1 | 6/2010 | Agresti et al. |
| 2011/0261164 | A1 | 10/2011 | Olesen et al. |
| 2012/0329038 | A1 | 12/2012 | Ismagilov et al. |
| 2014/0087386 | A1 | 3/2014 | Chiu et al. |
| 2017/0175174 | A1 | 6/2017 | Chiu et al. |

FOREIGN PATENT DOCUMENTS

| | | |
|---|---|---|
| CN | 1974751 A | 6/2007 |
| JP | 2017519484 A | 7/2017 |
| WO | WO-2009003184 A1 | 12/2008 |
| WO | WO-2010111265 A1 | 9/2010 |
| WO | WO-2012100198 A2 | 7/2012 |
| WO | WO-2012135667 A1 | 10/2012 |
| WO | WO-2015157369 A1 | 10/2015 |

OTHER PUBLICATIONS

CN201580029257.2 Office Action dated Mar. 4, 2019.
JP2013-550633 Office Action dated Jul. 14, 2016.
European search report with written opinion dated Sep. 26, 2018 for EP application No. 18184052.
Kumaresan et al., High-throughput single copy DNA amplification and cell analysis in engineered nanoliter droplets, Anal Chem. 80.10 (2008): 3522-9.
Mazutis et al., Droplet-Based Microfluidic Systems for High-Throughput Single DNA Molecule Isothermal Amplification and Analysis, Anal Chem 81(12):4813-4821 (2009).
Office action dated Jan. 4, 2017 for CN Application No. 201280012684.6.
Office action dated Jun. 23, 2016 for CN Application No. 201280012684.6.
Office action dated Oct. 2, 2018 for U.S. Appl. No. 15/301,798.
Chinese office action dated Oct. 10, 2015 for CN Application No. 201280012684.6.
Cohen, et al., Self-Digitization of Sample Volumes, Anal Chem. Jul. 1, 2010; 82(13): 5707-5717.
Dube, et al. Mathematical analysis of copy number variation in a DNA sample using digital PCR on a nanofluidic device. PLoS One. Aug. 6, 2008;3(8):e2876. doi: 10.1371/journal.pone.0002876.
European examination report dated Aug. 3, 2015 for EP Application No. 12736553.4.
European search report and opinion dated Apr. 17, 2014 for EP Application No. 12736553.4.
"Extended European Search Report and Search Opinion dated Nov. 9, 2017 for European Patent Application No. EP15776098.4".
Gansen, et al. Digital LAMP in a sample self-digitization (SD) chip. Lab Chip. Jun. 21, 2012;12(12):2247-54. doi: 10.1039/c21c21247a. Epub Mar 7, 2012.

(Continued)

*Primary Examiner* — David C Thomas

(74) *Attorney, Agent, or Firm* — Christensen O'Connor Johnson Kindness PLLC

(57) ABSTRACT

Methods, devices and systems for performing digital measurements are provided.

27 Claims, 17 Drawing Sheets

Specification includes a Sequence Listing.

(56) References Cited

OTHER PUBLICATIONS

Hanson, et al. Nanoscale double emulsions stabilized by single-component block copolypeptides. Nature. Sep. 4, 2008;455(7209):85-8. doi: 10.1038/nature07197.
Hindson, et al. High-throughput droplet digital PCR system for absolute quantitation of DNA copy number. Anal Chem. Nov. 15, 2011;83(22):8604-10. doi: 10.1021/ac202028g. Epub Oct. 28, 2011.
International preliminary report on patentability dated Aug. 1, 2013 for PCT/2012/022081.
International search report and written opinion dated Jul. 8, 2015 for PCT/2015/024840.
International search report and written opinion dated Aug. 7, 2012 for PCT/2012/022081.
Japanese Office Action dated Jun. 15, 2018 for JP Application No. 2016221388 (with English Translation).
Kreutz, et al. Theoretical design and analysis of multivolume digital assays with wide dynamic range validated experimentally with microfluidic digital PCR. Anal Chem. Nov. 1, 2011;83(21):8158-68. doi: 10.1021/ac201658s. Epub Oct. 7, 2011.
Lieber, Statistical Significance and Statistical Power in Hypothesis, J. Orthopaedic Research 8, 304-309.
Nakano et al. Single-molecule PCR using water-in-oil emulsion. Journal of Biotechnology. 2003;102(2):117-24.
"Office action dated Jan. 4, 2017 for CN Application No. 201580029257.2".
"Office action dated Apr. 8, 2016 for EP Application No. 12736553.4".
"Office action dated May 22, 2017 for U.S. Appl. No. 15/230,162".
"Office action dated Jun. 23, 2016 for CN Application No. 201580029257.2".
"Office Action dated Nov. 13, 2017 for U.S. Appl. No. 15/301,798".
"Office Action dated Nov. 14, 2017 for JP Patent Application No. 2016-221388".
"Office Action dated Dec. 5, 2017 for U.S. Appl. No. 15/230,162".
Penfold, et al. Quantitative imaging of aggregated emulsions. Langmuir. Feb. 28, 2006;22(5):2005-15.
"Pinheiro et al., Evaluation of a Droplet Digital Polymerase Chain Reaction Format for DNA Copy Number Quantification, Analytical Chemistry, Jan. 17, 2012, 84(2):1003-11".
Schneider, et al. The potential impact of droplet microfluidics in biology. Anal Chem. Apr. 2, 2013;85(7):3476-82. doi: 10.1021/ac400257c. Epub Mar. 15, 2013.
Shen, et al. Multiplexed quantification of nucleic acids with large dynamic range using multivolume digital RT-PCR on a rotational SlipChip tested with HIV and hepatitis C viral load. J Am Chem Soc. Nov. 9, 2011;133(44):17705-12. doi: 10.1021/ja2060116. Epub Oct. 13, 2011.
Sykes, et al. Quantitation of targets for PCR by use of limiting dilution. Biotechniques. Sep. 1992;13(3):444-9.
"U.S. Appl. No. 15/230,162 Notice of Allowance dated Jan. 26, 2018".
"U.S. Appl. No. 15/301,798 Office Action dated Feb. 16, 2018".
Yan. Image analysis and platform development for automated phenotyping in cytomics, Doctoral Dissertation, Leiden University, Nov. 27, 2013 (Nov. 27, 2013), pp. 1-132. Retrieved from the Internet<https://openaccess.leidenuniv.nl/bitstream/handle/1887/22550/PROEF.KUANYAN.THESIS.pdf?sequence=18>.
Zeng, et al. High-performance single cell genetic analysis using microfluidic emulsion generator arrays. Anal Chem. Apr. 15, 2010;82(8):3183-90. doi: 10.1021/ac902683t.

FIG. 13A          FIG. 13B                    FIG. 13C
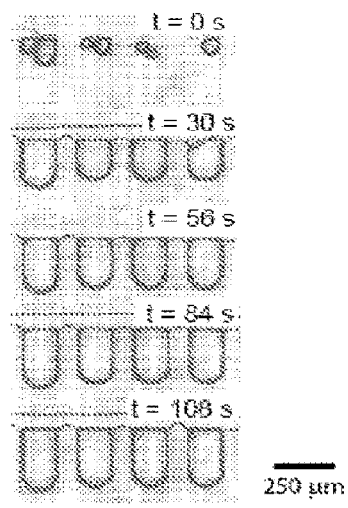
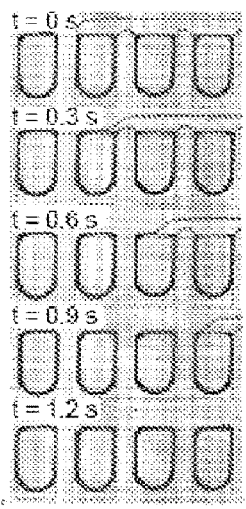
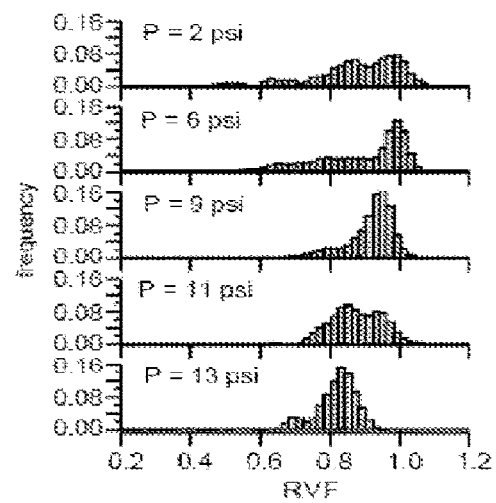
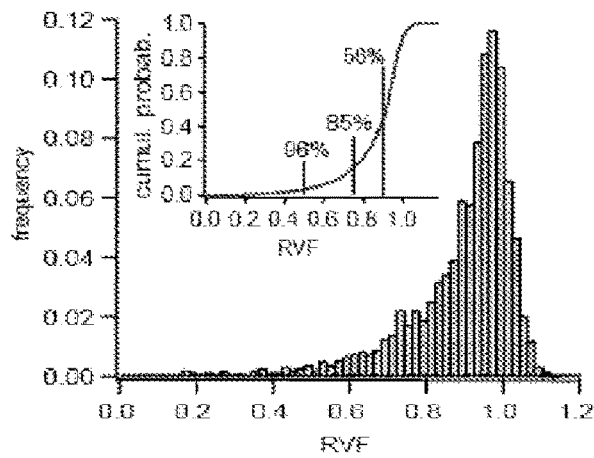
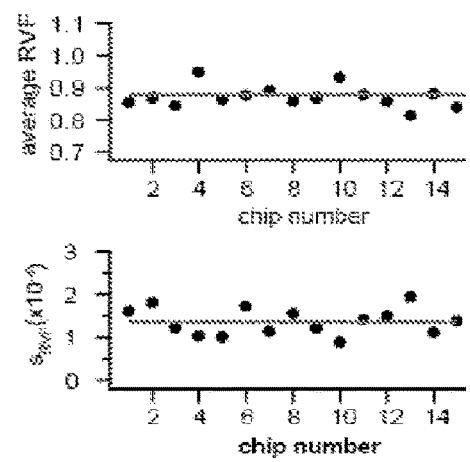
FIG. 13D                          FIG. 13E FIG. 15A
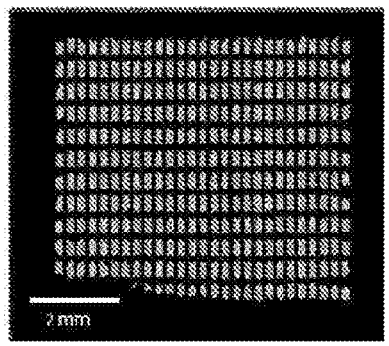
FIG. 15B
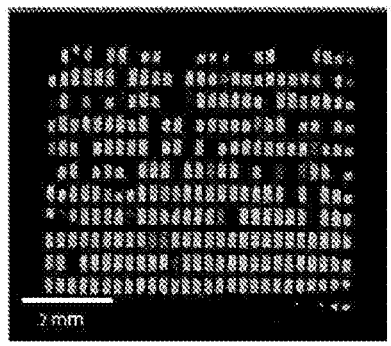
FIG. 15C
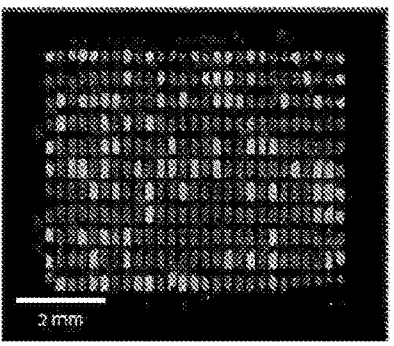
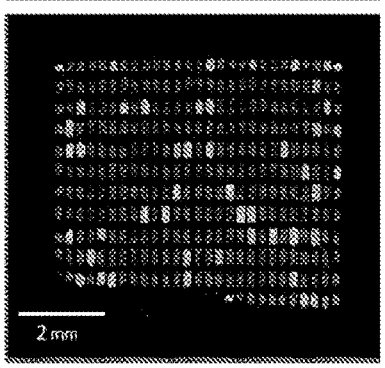
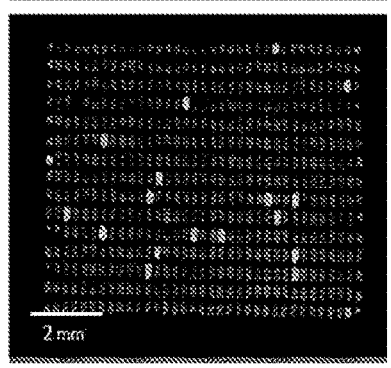
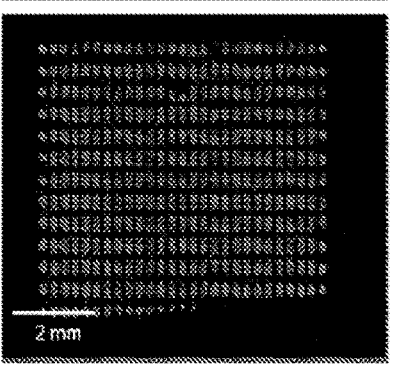
FIG. 15D          FIG. 15E          FIG. 15F FIG. 16A
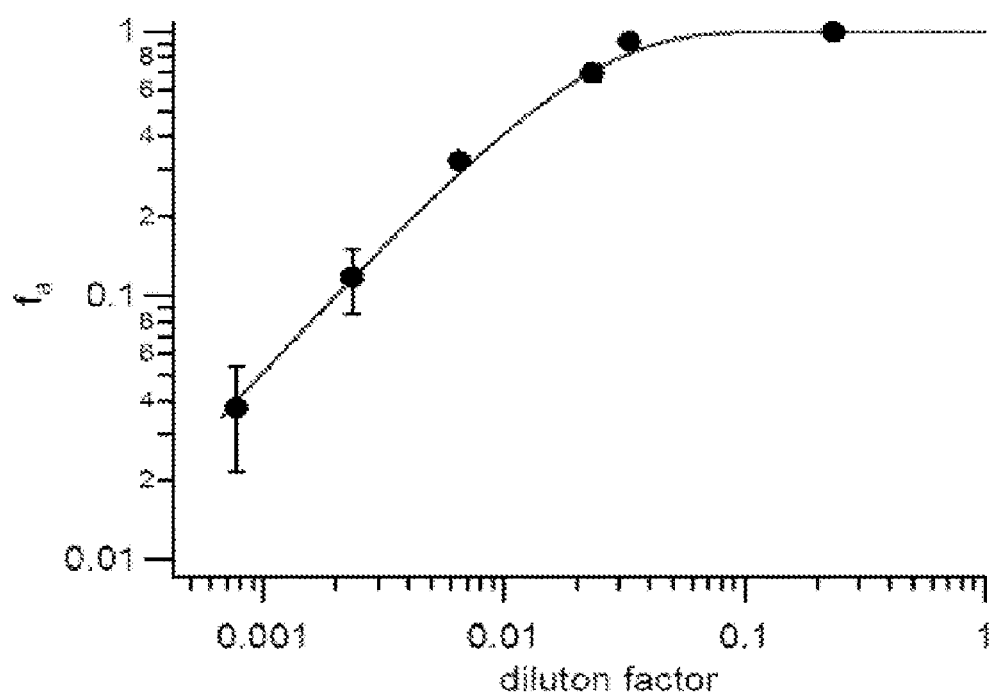
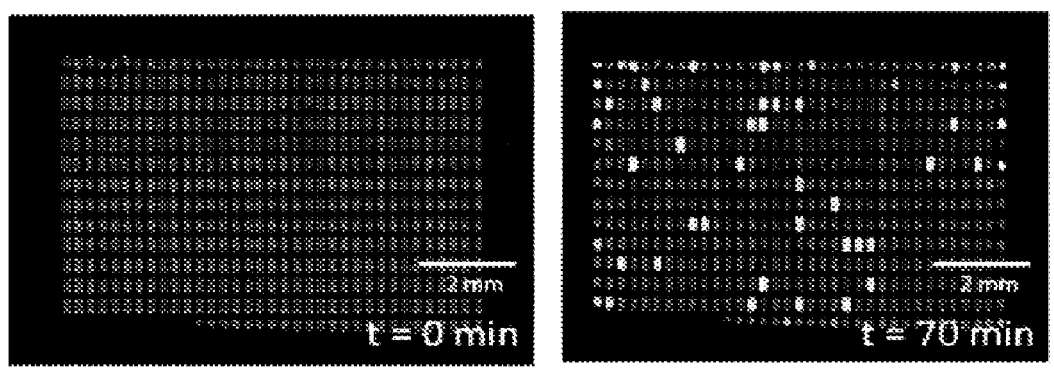
FIG. 16B Comparison of Confidence levels estimated from Z-test and from simulation

| | Z Method | | | | P Method | | |
|---|---|---|---|---|---|---|---|
| ($C_{S1} = 2.0 \times 10^{-5}$ molec/fL) | | ($C_{S2} = 2.2 \times 10^{-5}$ molec/fL) | | | | | |
| $C_1^{(a)}$ | $\sigma_1^{(b)}$ | $C_2^{(a)}$ | $\sigma_1^{(b)}$ | $(1-\alpha)^{(c)}$ | $\bar{C}^{(d)}$ | $\sigma_{\bar{C}}^{(e)}$ | $(1-\alpha)^{(c)}$ |
| $2.106 \times 10^{-5}$ | $9.09 \times 10^{-7}$ | $2.108 \times 10^{-5}$ | $8.52 \times 10^{-7}$ | 0.011 | $2.11 \times 10^{-5}$ | $9.11 \times 10^{-7}$ | 0.012 |
| $2.04 \times 10^{-5}$ | $8.24 \times 10^{-7}$ | $2.05 \times 10^{-5}$ | $8.40 \times 10^{-7}$ | 0.063 | $2.05 \times 10^{-5}$ | $7.98 \times 10^{-7}$ | 0.066 |
| $2.16 \times 10^{-5}$ | $8.97 \times 10^{-7}$ | $2.18 \times 10^{-5}$ | $8.70 \times 10^{-7}$ | 0.097 | $2.17 \times 10^{-5}$ | $9.26 \times 10^{-7}$ | 0.074 |
| $2.11 \times 10^{-5}$ | $8.74 \times 10^{-7}$ | $2.13 \times 10^{-5}$ | $8.74 \times 10^{-7}$ | 0.084 | $2.12 \times 10^{-5}$ | $8.55 \times 10^{-7}$ | 0.104 |
| $2.09 \times 10^{-5}$ | $8.71 \times 10^{-7}$ | $2.10 \times 10^{-5}$ | $8.82 \times 10^{-7}$ | 0.106 | $2.10 \times 10^{-5}$ | $8.47 \times 10^{-7}$ | 0.140 |
| $1.95 \times 10^{-5}$ | $7.94 \times 10^{-7}$ | $2.12 \times 10^{-5}$ | $8.39 \times 10^{-7}$ | 0.842 | $2.03 \times 10^{-5}$ | $8.56 \times 10^{-7}$ | 0.816 |
| $2.13 \times 10^{-5}$ | $8.73 \times 10^{-7}$ | $2.30 \times 10^{-5}$ | $9.98 \times 10^{-7}$ | 0.813 | $2.22 \times 10^{-5}$ | $9.27 \times 10^{-7}$ | 0.836 |
| $2.03 \times 10^{-5}$ | $8.23 \times 10^{-7}$ | $2.21 \times 10^{-5}$ | $9.18 \times 10^{-7}$ | 0.864 | $2.12 \times 10^{-5}$ | $8.57 \times 10^{-7}$ | 0.844 |
| $2.13 \times 10^{-5}$ | $8.59 \times 10^{-7}$ | $2.32 \times 10^{-5}$ | $1.00 \times 10^{-6}$ | 0.853 | $2.23 \times 10^{-5}$ | $9.20 \times 10^{-7}$ | 0.848 |
| $2.23 \times 10^{-5}$ | $9.18 \times 10^{-7}$ | $2.43 \times 10^{-5}$ | $1.03 \times 10^{-6}$ | 0.852 | $2.33 \times 10^{-5}$ | $9.69 \times 10^{-7}$ | 0.848 |
| $1.91 \times 10^{-5}$ | $8.09 \times 10^{-7}$ | $2.09 \times 10^{-5}$ | $8.57 \times 10^{-7}$ | 0.876 | $2.00 \times 10^{-5}$ | $8.40 \times 10^{-7}$ | 0.848 |
| $1.96 \times 10^{-5}$ | $8.08 \times 10^{-7}$ | $2.31 \times 10^{-5}$ | $9.81 \times 10^{-7}$ | 0.995 | $2.13 \times 10^{-5}$ | $8.96 \times 10^{-7}$ | 0.990 |
| $2.07 \times 10^{-5}$ | $8.46 \times 10^{-7}$ | $2.42 \times 10^{-5}$ | $9.91 \times 10^{-7}$ | 0.994 | $2.24 \times 10^{-5}$ | $9.68 \times 10^{-7}$ | 0.990 |
| $1.95 \times 10^{-5}$ | $7.87 \times 10^{-7}$ | $2.30 \times 10^{-5}$ | $9.63 \times 10^{-7}$ | 0.995 | $2.12 \times 10^{-5}$ | $8.58 \times 10^{-7}$ | 0.994 |
| $1.92 \times 10^{-5}$ | $7.97 \times 10^{-7}$ | $2.29 \times 10^{-5}$ | $9.61 \times 10^{-7}$ | 0.997 | $2.11 \times 10^{-5}$ | $8.66 \times 10^{-7}$ | 0.996 |
| $1.92 \times 10^{-5}$ | $7.58 \times 10^{-7}$ | $2.29 \times 10^{-5}$ | $9.64 \times 10^{-7}$ | 0.997 | $2.10 \times 10^{-5}$ | $8.71 \times 10^{-7}$ | 0.998 |

(a) Best fit concentration.
(b) Standard deviation of the $N_Z$ Z method simulations (see text for details).
(c) Confidence
(d) Average of best fit concentrations.
(e) Standard deviation of the $N_P$ P method simulations (see text for details). This standard deviation is not used in the P method and is provided simply for comparison with the values of the standard deviation used in the Z method.

FIG. 17

METHODS AND SYSTEMS FOR PERFORMING DIGITAL MEASUREMENTS

CROSS-REFERENCES TO RELATED APPLICATIONS

The present application is a continuation of U.S. patent application Ser. No. 15/230,162, filed Aug. 5, 2016, which is a divisional application of U.S. National Phase application Ser. No. 13/980,457, filed Dec. 9, 2013, now U.S. Pat. No. 9,428,793, which is a U.S. National Phase Application under 35 U.S.C. § 371 of International Application No. PCT/US2012/022081, filed Jan. 20, 2012, which claims the benefit of U.S. Provisional Application No. 61/434,670, filed Jan. 20, 2011, which are expressly incorporated herein in their entirities for all purposes.

BACKGROUND OF THE INVENTION

The present invention relates to methods, devices and systems for performing digital measurements. More specifically, the present invention relates to methods, devices and systems for performing digital measurements in varying volumes.

Digital measurements are becoming increasingly more important in biology, owing to their robustness, higher sensitivity and higher accuracy that they offer. In addition, unlike analog measurements, where the measurement often must be calibrated with a running standard, digital measurements, based on counting of binary yes or no responses, do not require calibration and thus save user time, enhance robustness and ease of the assay.

An important application for digital assays is the accurate quantification of DNA or RNA that is present in a sample. Here, the most widely used method to detect DNA or RNA is the polymerase chain reaction (PCR), where the sample is usually cycled between two or three temperatures around 60° C. and 95° C. The use of PCR to amplify DNA or RNA has greatly advanced a wide range of disciplines, ranging from basic biology to clinical diagnostics and forensics. One particular form of PCR that is often used in diagnostics and biomedical research is quantitative PCR (qPCR), which not only detects the presence of DNA or RNA in the sample, but also provides an accurate measure of its concentration. This is an important data point for making subsequent decisions and analysis—for example, the amount of a HIV therapeutic drug, that is given to the patient, is determined by the amount of detected viral RNA load in the test sample.

So far, the most common form to carry out qPCR is real-time PCR, which is widely used in many areas, including basic biomedical research and clinical diagnostics. In real-time PCR, the absolute concentration of a sample is inferred from the time evolution of the amplification process, which is monitored with a fluorescent probe, such as a molecular beacon or Taqman® probe, that specifically recognizes the amplification product. Real-time PCR is susceptible to various errors, including the formation of unwanted primer dimers, where primer molecules attach to each other because of complementary stretches in their sequence. As a result, a by-product is generated which competes with the target element for available PCR reagents, thus potentially inhibiting amplification of the target sequence and interfering with accurate quantification. The quantification of target also requires the precise knowledge of the amplification efficiency for each cycle, and because the growth is exponential, tiny uncertainties in amplification efficiency (e.g. below the threshold detection level) will result in very large errors in the determination of target copy numbers. This error can become very large when the initial concentration of nucleic acid is low or when the fluorescent detection is not sufficiently sensitive. Despite its power to identify and quantify target DNA from complex samples, real time PCR suffers from the inability to quantify low sample concentrations with sufficient precision, as required for example in the detection of pathogens or clinical diagnostics.

To overcome the difficulties of real-time PCR to quantify low copy-number DNA, digital or limiting dilution DNA amplification has been developed, which can quantify the absolute number of template copies in the sample more accurately. In dPCR, the total sample is divided into an array of small volumes, such that, based on Poisson statistics, only few volumes contain one or more target molecules, while the majority of volumes contains no DNA. DNA amplification is then carried out in all volumes simultaneously and results in an increase of fluorescence in only those few volumes that contain target molecules. The DNA copy number is easily and accurately determined by counting the number of fluorescent volumes (i.e. those that contain a copy of DNA).

The concept of dPCR is appealing, but it is not yet widely used because (1) it can be difficult to create a large array of very small volumes (picoliters to nanoliters) used for dPCR, and (2) the dynamic range of the experiment is defined by the size and number of discrete arrays and is often very low. In order to accurately quantify the amount of DNA or protein in the sample most of the compartments typically contain at maximum one target molecule. This implies that the initial concentration of sample be matched to the dynamic range of the assay. In other words, the initial sample concentration should be determined before inputting the correct concentration of sample into the device to run dPCR. This adds to the inconvenience of running dPCR and limits the potential of digital arrays with constant volumes.

Regardless of the particular reaction used, it is important to overcome the limited dynamic range of the digital assay. A straightforward way is to extend the scope of the assay by increasing the number of digitized volumes of the same size. This approach is problematic; in order to accommodate a large number of volumes, the device has to be large and would involve fairly complex and expensive microfabrication. Thus, there is a need for additional methods and systems for performing digital measurements.

Besides the above mentioned practical issues of dPCR, widespread use of the method can also be impeded by precise temperature control and temperature cycling. Generally, the temperature for the annealing and melting step is controlled within +/−1 degree Celsius. For many applications, where absolute quantification of DNA and RNA is important, these factors are difficult to meet or expensive to realize, in particular in resource-limited settings and at the point-of-care. To provide more ergonomic ways to amplify DNA and RNA in these settings, several isothermal methods have been developed, including rolling circle amplification (RCA), nucleic acid sequence based amplification (NASBA) or loop-mediated amplification (LAMP).

LAMP is an isothermal process for amplifying DNA or RNA with very high specificity at a fixed temperature between 60-65 degrees Celsius. Due to its high specificity it is able to discriminate single nucleotide differences during amplification. As a result, LAMP has been applied for SNP (single nucleotide polymorphism) typing. LAMP has also been shown to detect viral RNA with about ten-fold higher sensitivity than RT-PCR. Another feature, that differentiates LAMP from other isothermal methods, is the ability to directly correlate the amplification of DNA with the production of magnesium pyrophosphate, which increases the turbidity of the solution. The progress of the LAMP solution can thus be followed with a simple turbidimeter. Therefore, a non-homogeneous assay can be used for detecting the amplification products that result from LAMP. The production of magnesium pyrophosphate can also be used in form of a fluorescent indicator, which is particularly useful for digital assay readout. Before the reaction, a small amount of Calcein is added to the reaction mix. During amplification, the increased production of pyrophosphate leads to a sharp increase in Calcein fluorescence in those volumes that contain one or more target molecules.

These reactions proceed at a fixed temperature, which reduces instrument complexity and lowers energy consumption, making them more suitable for point-of-care diagnostics and home-medicine devices. Translation of these methods into a digital format is an important step towards a better and more accurate detection of pathogens at the point-of-care. Moreover, digital assays would also improve the accuracy of protein amplification based assays, such as ELISA (Enzyme-Linked-Immunoadsorbent-Assay) or any single molecule based assay, where the single molecule assay may or may not require amplification.

In view of the above, there is a need to provide improved methods and systems for performing digital measurements. In addition, there is also a need to provide additional techniques using digital measurements, such as digital LAMP. The present invention disclosed herein provides these needs and more.

BRIEF SUMMARY OF THE INVENTION

The present invention provides methods, devices and systems for performing digital measurements. More specifically, the present invention relates to methods, devices and systems for performing digital measurements in varying volumes. In some aspects, the present invention provides methods and apparatus for increasing the dynamic range of digital measurements, including but not limited to digital PCR, digital isothermal nucleic acid amplifications (e.g. digital NASBA and digital LAMP), digital protein amplification (e.g. digital ELISA), digital single-molecule measurements, and other forms of digital measurements.

In one aspect, the invention provides a method for increasing the dynamic range of digital measurements of a sample comprising:
 creating a sample concentration gradient; and/or
 creating sample volumes of different sizes.

In one embodiment, the dynamic range is increased by integrating digital measurement and readout with methods and apparatus for the formation of a concentration gradient. The concentration gradient of analyte molecules is preferably logarithmic or exponential in shape, although a number of other shapes are possible, including but not limited to linear, polynomial, error, Gaussian, exponential, logarithmic, and any combinations thereof.

In another embodiment, the dynamic range is increased by using digitized volumes of varying sizes. For example, the dynamic range may be increased by having on the same chip or substrate one set of array of digitized volumes that are 100 nL in volume, a second set of array that is 10 nL, a third set of array that is 1 nL, a fourth set of array that is 100 pL, a fifth set of array that is 10 pL, a sixth set of array that is 1 pL, a seventh set of array that 100 fL, an eighth set of array that is 10 fL, and finally a ninth set of array that 1 fL. It may not be necessary to have all these sets of array on the same chip, depending on the final application. For some application, arrays that span 1 fL to 1 nL may be sufficient; for other applications, arrays that span 100 nL to 1 pL may be more appropriate. Yet for other applications, only two sets of arrays with two sets of differing volumes may be sufficient. The number of sets of arrays that contain different volumes will vary, and will depend on the size of each array. For example if a set of array contains one million digitized volumes, then it may not be necessary to have arrays of 1 nL, 100 pL, 10 pL and 1 pL to span the concentration range of pL to nL, and simply two sets of arrays of 100 pL and 1 pL may be sufficient.

In another aspect, the use of concentration gradients and varying sizes of digitized volumes can be combined to further increase the dynamic range of the digital measurement. In another aspect, the invention is a method for increasing the dynamic range of digital single-molecule measurements of a sample using a concentration gradient or discrete volumes of different sizes. In another aspect, the invention is a process of preparing a patterned surface with hydrophobic and hydrophilic patches, wherein said patches cause the formation of wetted droplets of different size sample volumes. In another aspect, the invention is non-transitory computer-readable medium having computer executable instructions stored thereon, the instructions for a machine to carry out any of the methods described herein. In another aspect, the invention is an array comprising a patterned surface with hydrophobic and hydrophilic patches, wherein said patches cause the formation of wetted droplets of different size sample volumes. In another aspect, the invention is used to increase the dynamic range of digital measurements of a sample in a non-homogeneous assay. It is important to note that there are a number of methods for forming concentration gradients as well as for digitizing sample volumes. The examples provided herein should not be considered limiting.

This invention also describes methods and apparatus for carrying out the following: (1) digital NASBA, (2) digital LAMP, (3) Performing PCR or other nucleic acid amplification using surface-attached droplet formed using a surface patterned with hydrophobic and hydrophilic patches, and (4) Performing readout of digital nucleic acid amplification using a non-homogeneous assay.

In yet another aspect, the present invention provides a method for using digital measurements to determine a concentration of a sample. The method can include producing a first plurality of droplets having a first volume distribution, wherein at least one of the droplets of the first plurality contains contents from the sample; analyzing a second plurality of droplets having a second volume distribution to determine individual volumes of the droplets in the second plurality and a number of droplets in the second plurality that contain a detectable agent, wherein the first volume distribution is the same or different than the second volume distribution; and using individual volumes of the droplets in the second plurality and the number of droplets in the second plurality that contain the detectable agent to determine the concentration of the sample.

In yet another aspect, the present invention provides a system for conducting digital measurements of a sample. The system can include a sample holder containing a first plurality of droplets having a first volume distribution; a detector for detecting a detectable agent contained in at least one droplet of the first plurality; and a computer comprising a memory device with executable instructions stored thereon, the instructions, when executed by a processor, cause the processor to: analyze a second plurality of droplets having a second volume distribution to determine individual volumes of the droplets in the second plurality and a number of droplets in the second plurality that contain a detectable agent, wherein the first volume distribution is the same or different than the second volume distribution; and use individual volumes of the droplets in the second plurality and the number of droplets in the second plurality that contain the detectable agent to determine the concentration of the sample.

In yet another aspect, the present invention provides a method for performing digital loop-mediated amplification of a sample. The method can include producing a plurality of droplets of the sample on a microfluidic device, wherein at least one droplet in the plurality comprises a nucleic acid molecule; and performing loop-mediated amplification in the at least one droplet to produce amplified product of the nucleic acid molecule.

For a fuller understanding of the nature and advantages of the present invention, reference should be had to the ensuing detailed description taken in conjunction with the accompanying drawings. The drawings represent embodiments of the present invention by way of illustration. The invention is capable of modification in various respects without departing from the invention. Accordingly, the drawings/figures and description of these embodiments are illustrative in nature, and not restrictive.

BRIEF DESCRIPTION OF THE DRAWINGS

FIG. 8A shows a dark field image of droplets on a silanized microscope slide. The size of individual droplets can be determined from a dark field image, if the droplets are well enough separated. The contrast arises from light that scatters from the interface between aqueous phase and oil giving the droplet a circular outline, from which the diameter of the droplet can be measured. The scale bar represents 100 microns. FIG. 8B shows a size distribution of 577 droplets measured after emulsification. The distribution is asymmetric with a median diameter of 20 µm. Most droplet diameters fall in the range between 10 and 40 microns.

FIGS. 11A and 11B depict images of droplets without target DNA after PCR (negative control experiment). Shown are combined dark field/ROX (11A)

and dark field/FAM (11B) images, where ROX is the reference dye added to the reaction and FAM is the fluorescence indicator used in the Taqman® probe to detect DNA amplification. The dark field illuminates the ring-shaped outline of the droplet, overlaid with the Gaussian shaped fluorescence signal from the fluorophore. The insets show the intensity measured along the light gray line through the droplet center. The signal in the center region of the droplet is mostly due to fluorescence; in the absence of DNA target the center region remains dark, the ratio between ROX and FAM fluorescence is high (ROX:FAM=120:20=6:1). FIGS. 11C and 11D are after PCR images of droplets containing target DNA. The combined dark field/ROX (11C) and dark field/FAM (11D) images are shown with the corresponding line scans through the droplet. The line scan indicates an increased fluorescent signal in the center region as well as a Gaussian profile that was not observed in empty droplets. The respective ratio between the two fluorescent signals is significantly lower than for empty droplets (ROX:FAM=60:30=2:1).

FIG. 12A is a schematic diagram showing the individual components of a fully assembled chip. The microfluidic array can be embedded in a thin piece of PDMS, which can be covered by a sealant film on top and a PDMS coated cover slip on the bottom. Air pressure can be delivered via a removable adapter, which can be connected to an external pressure source. FIG. 12B is an example layout of the microfluidic network. A dense array of rectangular side chambers was connected to a thin main channel. The whole array was surrounded by a separate water reservoir to saturate the PDMS during incubation at 65° C. The scale bar represents 5 mm. FIG. 12C shows an example geometry of the side chamber array and main channel. All dimensions are in micrometers.

FIGS. 13A-13E show sample self-digitization in the dLAMP SD chip, in accordance with an example embodiment of the present invention. FIG. 13A provides sequential images showing the initial filling of the side-chamber array with aqueous solution. After priming the chip with oil, the aqueous sample entered the main channel and distributed itself into the side compartments, displacing the oil phase in the chambers. FIG. 13B provides a sequence of images showing the self-digitization of aqueous sample in the side chambers. After the whole aqueous phase entered the chip, the tailing oil phase in the main channel isolated individual nanoliter sized droplets in the side chambers. FIG. 13C shows dependence of the distribution of droplet size in the side chambers on applied pressure. The most uniform distribution with the highest average relative volume fraction (RVF) was obtained for an external pressure of 7 psi. Lower and higher pressures resulted in formation of droplets with more variable volumes and reduced RVF. FIG. 13D depicts a size distribution of RVF values for 5000 self-digitized droplets from 16 individual chips. The external pressure was set to 7 psi in all experiments. The average RVF of all droplets was 0.89±0.14. The inset shows the cumulative distribution of RVF values. The numbers correspond to the fraction of droplets with an RVF exceeding 50%, 75% and 90%, respectively. For example, 85% of all droplets filled out more than 75% of the chamber. FIG. 13E shows the reproducibility of sample self-digitization. Shown are the average RVF value and the standard deviation for 15 individual chips, each filled with 7-psi external pressure.

FIG. 14A shows an effect of incubation on droplet volume. Typical droplet-size distributions are shown before and after incubation at 65° C. for 70 minutes. The sample consisted of a negative control solution without template, hence no amplification was expected to occur. On average the droplets shrank by approximately 10%. As can be seen in the inset, the droplets located at the periphery of the array suffered from slightly increased shrinkage because they were more exposed to the bulk PDMS. Droplets in the center of the array were less affected by shrinkage. FIG. 14B shows a digital LAMP signature observed in our chip. A section of the chamber array is shown before and after incubation. The intensity profile corresponds to a line across the centers of several chambers. Loop mediated DNA amplification in some of the chambers caused a sharp increase in their fluorescence. Neighbouring, non LAMP-competent chambers showed no increase in fluorescence, which demonstrated that sample crosstalk between adjacent chambers was negligible.

FIGS. 15A-15F show digital LAMP results for different DNA template concentrations $c_i$: $c_i=c_0/4$ (15A), $c_i=c_0/30$ (15B), $c_i=c_0/150$ (15C), $c_i=c_0/430$ (15D) and $c_i=c_0/1300$ (15E). $c_0$ is the concentration of the template stock solution. The respective fraction of LAMP-competent chambers is analyzed in FIG. 16A. For the experiment at lowest sample concentration ($c_0/1300$), a 535-chamber chip was used to increase the absolute number of positive chambers. FIG. 15F shows a control experiment of a LAMP solution with no template added. As expected, none of the chambers showed an increase in fluorescence beyond background.

FIGS. 16A and 16B show quantification of relative and absolute changes in DNA concentration, in accordance with an example embodiment of the present invention. FIG. 16A shows a dilution series of the control DNA sample contained in the LoopAmp® kit, see FIGS. 15A-15F. For each sample concentration, at least three different chips were analyzed. The solid line represents the expected fraction of positive events based on a Poisson distribution for a template concentration of $0.99 \times 10^4$ molecules per µl, in the stock solution. This concentration was determined from the 3 lowest sample. FIG. 16B shows absolute quantification of DNA concentration. A 535 well chip is shown before and after incubation at 65° C. for 70 minutes. λ-phage DNA was diluted to a final concentration of 20 copies per for which we expected approximately 12% positive chambers. After incubation we detected 9.8% LAMP-competent droplets in the 535 well array (47 out of 479 initially formed droplets). The difference between expected and measured values for $f_a$ may have been caused by pipetting errors accumulated over the 8-fold dilution series.

FIG. 17 shows Table 2, which includes a comparison of confidence levels estimated from Z-test and from simulation.

DETAILED DESCRIPTION OF THE INVENTION

Figure 1:
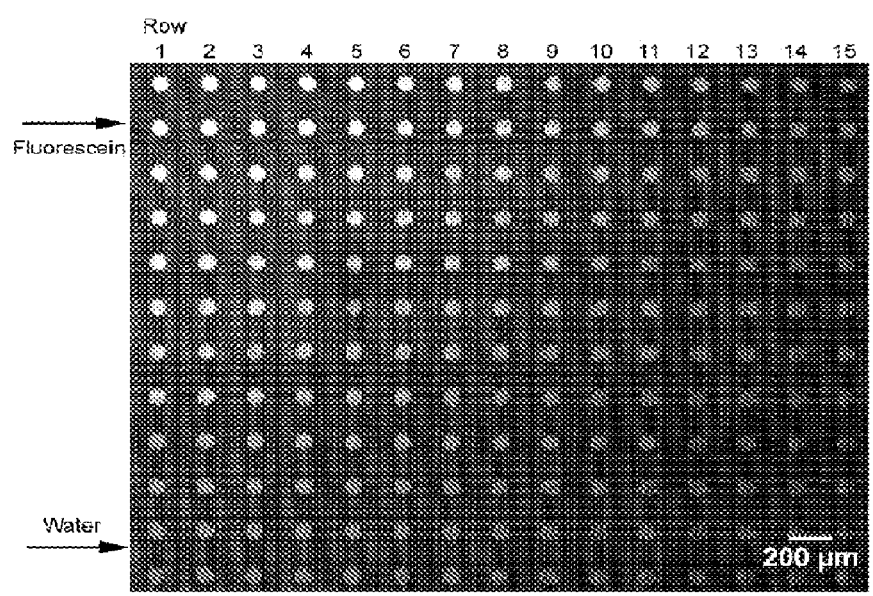
FIG. 1 depicts the generation of digitized volumes containing a gradient concentration of analytes. For visualization purposes, we used the fluorescent dye, fluorescein, as our analyte. We flow the gradient over an array of wells. Here, the gradient was generated using 200 µM fluorescein at 200 µL/min from a top inlet (top arrow) and water at 400 µL/min from a bottom inlet (bottom arrow). Once the wells have been filled with the concentration gradient, we flowed light mineral oil (which is less dense than water) over the wells to create individual digitized volumes within the wells. The wells in this example are of the same volume, but wells of varying volumes can also be used. For this experiment, the wells were 75 µm in diameter and 100 µm deep and sat beneath a 2 mm tall flow chamber.

The present invention relates to methods and systems for performing digital measurements. More specifically, the present invention relates to methods and systems for performing digital measurements in varying volumes.

I. General

While not limiting, the present invention is based in-part on increasing the dynamic range of a digital assay by generating volumes with variable size. For a given sample concentration, the size of the volumes can define the probability of being occupied by one or more molecules (e.g., template molecules) of interest. In the example of amplification-related techniques, variation of volume size can be used to alter this occupational probability and thus the number of wells or sample volumes (e.g., droplets) that show amplification. Notably, the present invention is better than existing techniques that simply increase the number of volumes with constant size so as to increase the dynamic range. This advantage is because the methods and systems disclosed herein do not require a large area to accommodate the volumes needed to expand dynamic range, which, e.g., increases the likelihood of defects on the chip where some digitized volumes do not form properly or have other defects. In addition, simply increasing the number of volumes also increases the time required to analyze all the digitized volumes.

Furthermore, the present invention provides methods, systems and devices for performing digital assays with increased dynamic range, where a large number of volumes of varying size is generated. Unlike the above mentioned prefabricated platforms, the present invention can include use of a distribution of sizes (e.g., volumes) that is continuous rather than discrete. In some embodiments, droplets of variable size can be created in various ways, either randomly or through controlled application of microfluidics. For example, microfluidic generation of constant volume droplets is well known in the art by using a T-junction or flow-focusing device. In these systems, the size of the droplet can be controlled by the shear rate and channel dimensions. If for a given T-junction geometry the shear rate is continuously varied, droplets of different volumes can be generated. These methods can be realized, e.g., by computer-controlled syringe pumps or modulated air pressure, which adjusts the relative flow speeds of the aqueous phase and the oil carrier fluid.

In some embodiments, droplets of various size can be generated randomly, by emulsification in a sample holder (e.g., a test tube). Droplet randomness can simplify the experiment because, e.g., no efforts need be made to control the size of droplets. During emulsification, droplets of different volume can be stabilized with the use of different surfactants. The emulsification approach is particularly useful for several reasons: (1) the method is compatible with basic instrumentation found in every biomedical laboratory, (2) droplet generation is simple; it does not require complex chip design or sophisticated equipment for flow control, (3) the droplets are not confined in individual wells, which minimizes the space required to accommodate a large number of droplets and (4) the assay is simple because the same container can be used for droplet generation and droplet storage during amplification. No sample transfer is needed between droplet generation and the amplification reaction.

The term "dynamic range" is defined as the ratio between the largest and smallest possible values of a changeable quantity.

The term "digitized volumes" refers to the volumes produced after obtaining an initial sample and separating it into physically distinct smaller volumes in preparation for an assay.

The term "homogeneous assay" is defined where all assay components exist in solution phase at the time of detection. In a homogeneous assay, no component of the assay scatters detectable light.

The term "non-homogeneous assay" is defined where one or more assay components are present in solid phase at the time of detection. Formation of a precipitate or particulate, such as in LAMP or rolling circle amplification, is a common form of a heterogeneous assay. In this type of assay, the solid phase components may scatter detectable light.

As provided herein, the term "a continuous volume distribution" is intended to describe a distribution of volumes that vary continuously, rather than by pre-defined discrete steps, across the volume distribution. For example, chip-based platforms can include well or droplet volumes that over a volume distribution defined by pre-defined, discrete steps fabricated as part of the chip. That is, a chip can be made to have volumes present at 100 nL, 10 nL, and 1 nL, with no other volumes present in between those discrete steps. In contrast, a continuous volume distribution in not pre-defined (i.e., the volume distribution is undefined prior to producing or forming droplet volumes). The continuous volume distributions can, for example, be produced via emulsification, as described further herein. In emulsions, the volumes (e.g., droplet volumes) have a discrete volume but the droplet volumes in the distribution are undefined prior to producing the droplets (i.e., not pre-defined by fabrication techniques) and the volumes are randomly distributed along the continuous volume distribution. An upper and lower boundary for droplet volumes can be modified by the forces imparted on the emulsion (e.g., by the speed of vortexing or the intensity of shaking). However, the droplet volumes generated by such techniques continuously vary along the volume distribution produced.

In some aspects, continuous volume distributions can also be characterized such that for any set (or plurality) of droplet volumes, its distribution function can be denoted f(x), where f(x)dx is the probability that a given droplet in the set will have a volume between x and x+dx. (dx is an infinitesimally small number.) In certain embodiments, a continuous distribution is one where the volumes of the droplets in the droplet set are (1) not pre-specified and (2) that for some range $x_{lower} < x < x_{upper}$, f(x) is always greater than zero ($x_{lower}$ cannot be equal to $x_{upper}$, and nothing more needs to be known about f(x)). Thus, the present invention can in some embodiments include using a droplet set drawn from a continuous distribution, measuring the volume of each droplet in the set and using the measured droplet volumes in analysis.

I. Methods for Digital Measurements

In one embodiment, the present invention provides a method for creating concentration gradients that are integrated with digital measurement and readout. For example, one might integrate microfluidic gradient generation with a sample digitization chip. FIG. 1 shows an example of concentration gradients formed using microchannel inlets. For increasing the dynamic range, a logarithmic or exponential concentration gradient is preferred, but a number of methods are now available for forming various types and shapes of concentration gradients on chip, including non-linear gradients such as power, exponential, error, Gaussian, and cubic root functions. FIG. 1 depicts the generation of digitized volumes containing a gradient concentration of analytes.

To form a concentration gradient using the type of microfluidic design shown in FIG. 1, there needs to be only 2 inlet reservoirs or channels, but more would also be suitable for use of the invention. One inlet is used for the sample and one for buffer (or PCR reagent in the case of digital PCR). As the two solutions flow through the network, the sample solution becomes diluted by the buffer (water or PCR reagent) solution in a pre-defined fashion such that at each of the outlet channels, a different concentration of the sample is present. Linear, polynomial, and logarithmic gradients spanning 6 orders of magnitude have all been generated using variations of this design.

In another embodiment, a logarithmic or exponential gradient spanning 6 orders of magnitude in concentration is used. The sample and PCR solution is pipetted into the two inlet reservoirs, after which they will pass over the array of wells. Once the wells have been filled with the concentration gradient, light mineral oil or some other immiscible fluid is flowed over the wells to create individual digitized volumes within the wells. The wells in this example are of the same volume. In another embodiment of the invention, the scheme depicted in FIG. 1 is used with wells of varying volumes.

In another embodiment, the sample and PCR solution is pipetted into the two inlet reservoirs, after which they will pass over an array of hydrophilic and hydrophobic patches. As the sample flows over the hydrophilic patches, they cause the formation of wetted droplets of different size sample volumes.

Figure 2:
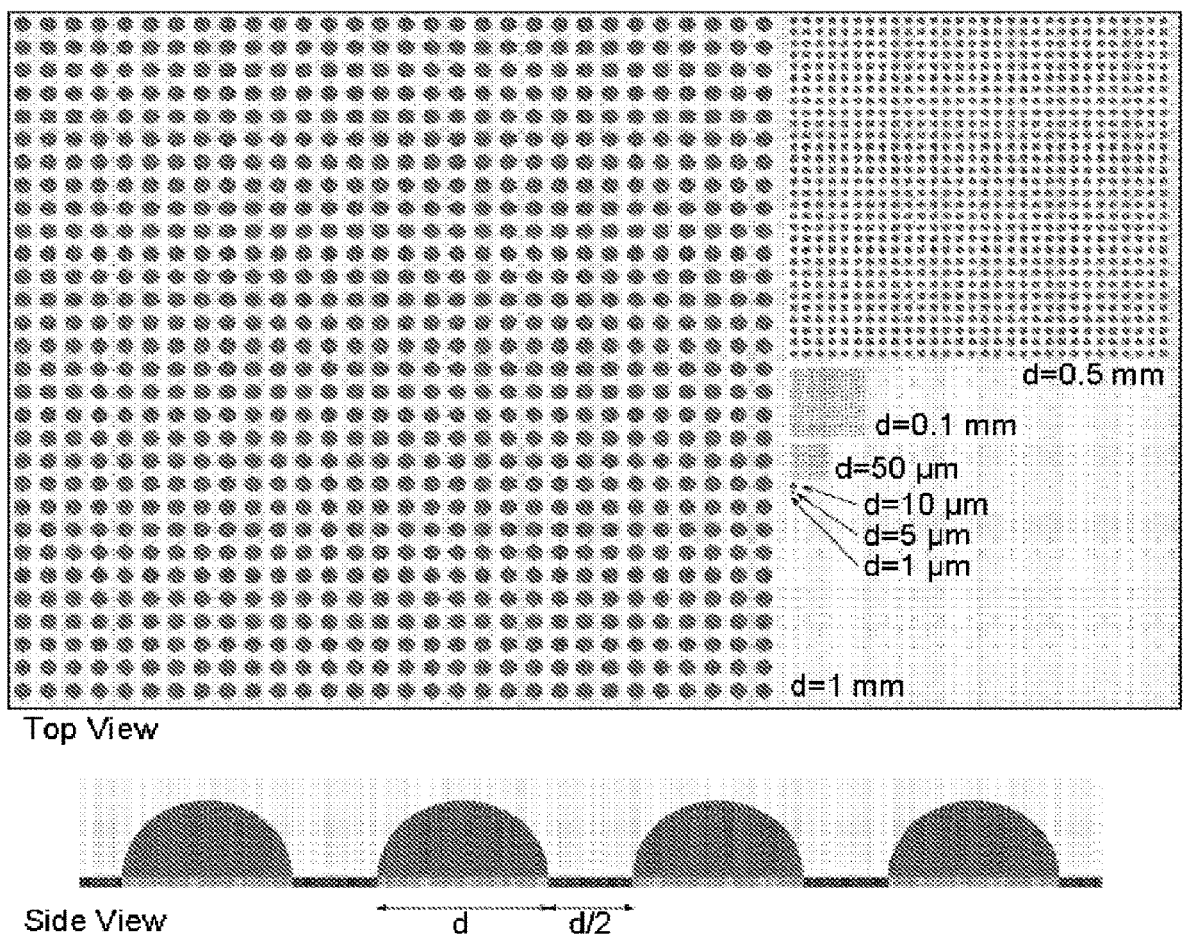
FIG. 2 depicts methods and apparatus for generating digitized volumes of varying sizes (volumes) using a hydrophobic and hydrophilic patterned surface. Here, hydrophilic patches that are circular in shape are patterned in a background of hydrophobic surface. When this surface is exposed to water (or any other aqueous solution, such as sample solution, PCR reagent solution, or buffer) and oil, the aqueous solution will prefer to wet the hydrophilic patches and the oil solution will prefer to wet the hydrophobic surface. As a result, droplets (or hemi-droplets) of aqueous solution will form on the hydrophilic patches surrounded by oil. Furthermore, the areas (e.g. area of the circle) of the hydrophilic patches are varied, such that the different size of the hydrophilic patch controls the volume of aqueous solution retained by the hydrophilic patches. The volume retained by the hydrophilic patch can have different cross sectional shapes even if the patches are circular. The exact shape will depend on the precise hydrophobic and hydrophilic surface used as well as the nature of the oil phase and the aqueous phase. The cross section shape can be hemispherical or more rounded or more pancaked than hemispherical. The hydrophilic patches are preferably circular, but can be a number of other shapes, including square and rectangular.

Alternatively, the sample can be digitized as shown using the pattered surface shown in FIG. 2.

In another aspect of the invention, the gradients are used in conjunction with digitized volumes created using valves, wells, or droplets. In the embodiment with droplets, the droplets can be formed in a continuous-flow fashion either in the T-channel geometry or in the flow focusing geometry, both of which are well known in the art.

To digitize the sample that had been diluted, the digitization scheme described in FIG. 1 can be used. Here, the sample solution containing different concentrations of target molecule are flown over the topographically patterned surface to form digitized and discrete volumes for subsequent digital measurements and readout. Alternatively, we can digitize the sample as shown using the patterned surface shown in FIG. 2.

In another embodiment, the sample can be digitized using microfluidic channels and immiscible fluid phases. In this embodiment, the sample phase is introduced into the channel, followed by an immiscible phase which forms discrete sample volumes that are defined by the geometric dimensions of the side cavities (D. E. Cohen, T. Schneider, M. Wang, D. T. Chiu *Anal. Chem.* 82, 5707-5717).

Another aspect of the invention comprises a device for carrying out the methods of the invention. Such devices may create concentration gradients that are integrated with digital measurement and readout. In another embodiment, the device carries out the method for increasing the dynamic range of digital measurements of a sample, comprising creating a sample concentration gradient; and/or creating sample volumes of different sizes.

In some embodiments, the present invention includes methods to increase the dynamic range of digital measurements that are based on creating arrays of digitized and discrete volumes of different sizes. This method is better than simply increasing the number of digitized volume so as to increase dynamic range. This is because simply increasing the number of digitized volumes increase the area the volumes occupy as well as increase the likelihood of having defects on the chip where some digitized volumes do not form properly or have other defects. Simply increasing the number of digitized volumes also increase the time required to analyze all the digitized volume. A better approach to increase the dynamic range is by creating arrays of digitized volumes of different sizes rather than simply increasing the number of digitized volumes. The arrays of digitized volumes of different sizes can be a random array (e.g. droplets of different diameters all present and distributed randomly in a container) or can be a regular array (e.g. those shown in FIG. 2).

FIG. 2 shows one example of creating arrays of digitized volumes of different sizes, where patterned surfaces are used to create arrays of volumes of different sizes. In this example, 7 sets of arrays are created, where each array contains 900 digitized volumes (30×30). The array is formed by creating hydrophilic circular patches in a background of a hydrophobic surface. As a result, when the surface is exposed to aqueous solution and oil, the hydrophilic patches will be covered by an aqueous drop surrounded by oil. The side view of the aqueous drop is shown at the bottom of the figure. This side view depicts a hemi-spherical drop, but the shape can change (either more pancaked or more rounded) depending on the exact surfaces we use and the oil and aqueous solution used. In one embodiment, a heavy oil is used, and the drop will be more pancaked because the oil will push on the drop.

The circles that define each set of the 900 hydrophilic patches have different sizes, ranging from 1 μm in diameter to 5 μm to 10 μm to 54 μm to 100 μm to 500 μm and finally to 1 mm in diameter. Because the volume of the drop scales roughly as cubic to the diameter of the drop, increasing the diameter of the patch by 10 times increases the volume by about 1,000 times. As a result, using digitized volumes of varying sizes is more efficient in terms of space and readout than simply using more digitized volumes of the same size. In one embodiment, 900 digitized volumes for each set of the array is used because this number is suitable for arriving at a statistically robust digital readout. However, depending on the particular application and the needed robustness of the readout, either more digitized volumes within each set of array or less digitized volumes can be designed.

The use of this design represents a unique scheme for creating a large array of digitized volumes with varying sizes due to the ease of surface patterning hydrophilic patches of different sizes. Therefore, for applications such as digital PCR where a wide dynamic range is often desired, it is highly beneficial to perform PCR in drops that are created using patterned surfaces as described in FIG. 2.

In some embodiments, the present invention provides methods for using digital measurements to determine a concentration of a sample. The methods can include producing a first plurality of droplets having a first volume distribution, wherein at least one of the droplets of the first plurality contains contents from the sample; analyzing a second plurality of droplets having a second volume distribution to determine volumes of the droplets in the second plurality and a number of droplets in the second plurality that contain a detectable agent, wherein the first volume distribution is the same or different than the second volume distribution; and using volumes of the droplets in the second plurality and the number of droplets in the second plurality that contain the detectable agent to determine the concentration of the sample.

In some embodiments, the volumes can be created using valves, wells, or droplets. The embodiments that involve droplets may be particularly useful. Here, droplets of different volumes (diameters) can be generated using a wide range of methods. In one method, droplets of a defined volume are generated using microfluidics (e.g. with T-channel or flow focusing as well known in the art); by varying the shear rate or channel dimension, droplets of different sizes are easily formed. In another method, the droplets of different volumes are generated by emulsification with the aid of different surfactants; here the droplets of different volumes are stabilized and are controlled with the use of different surfactants. With either method, amplification of analyte (e.g. digital PCR) can be carried out simultaneously in all droplets of different volumes (sizes), after which the droplets can be flowed in a single-file format through a flow cytometer or other similar device where the size of the droplet can be determined and the fluorescence from the droplet can be interrogated. In this example device, the presence of amplification product in each droplet is determined based on fluorescence and the size (volume) of each droplet is determined based on the scattering signal from the droplet. In this way, by noting both the size of each droplet and the presence or absence of amplification product in each droplet of a given size, it is possible to back-calculate the original concentration of the analyte present in the sample after interrogating a sufficient number of droplets of different sizes. Because the droplets are of different sizes, for a given dynamic range, the analysis is much faster than if the droplets are all of a similar size for reasons discussed previously.

As described herein, the volumes can be produced having a variety of volume distributions, which can be analyzed using a variety of different methods. In some embodiments, a sample can contain a molecule or molecules of interest that can be analyzed. Discrete volumes of the sample can be generated for analysis via digital measurements. For example, the methods herein can include producing a plurality of droplets having a volume distribution. In some embodiments, the plurality of droplets of the sample can be produced in an emulsion that includes combining immiscible fluids, as further described herein. In one example, a sample can include an aqueous solution that includes a molecule of interest (e.g., a nucleic acid molecule). The sample can be mixed with an oil to form droplets of the sample suspended in the oil. Depending on the method used, the volumes of the plurality of droplets in the emulsion can be randomly distributed along a continuous volume distribution. Furthermore, the ranges of volumes can be controlled by the method used to form the emulsions. For example, intensity of vortexing, shaking, and/or sonicating can be controlled to produce a desired volume distribution.

As will be appreciated by one of ordinary skill in the art, the ranges for and volumes within a volume distribution will depend on a variety of factors for a given analysis. In some embodiments, the volume distributions of the plurality of droplets can include a volume range from about 100 nano liters (nL) to about 1 femtoliter (fL), from about 10 nL to about 10 fL, from about 1 nL to about 100 fL, from about 100 nL to about 1 picoliter (pL), from about 10 nL to about 10 pL, from about 1 nL to about 1 pL. Depending on the selected factors for producing droplets, it is routine to define the upper and lower boundaries of a volume distribution by, e.g., changing the intensity of mixing a sample and oil with a surfactant. There can be ranges of volumes in the volume distributions. For example, volumes in the distributions can range by more than a factor of 2, by more than a factor of 10, or by more than a factor of 100 and by other factors. By ranging by a factor of 2, the lower boundary of the volume distribution can be, e.g., 10 nL with an upper boundary of 20 nL. Similarly, By ranging by a factor 10, the lower boundary of the volume distribution can be, e.g., 10 nL with an upper boundary of 100 nL.

In addition to producing a first plurality of droplets having a first volume distribution, the present invention further includes analyzing a second plurality of droplets having a second volume distribution. Analyzing the second plurality of droplets can include, e.g., determining volumes of the droplets in the second plurality. This volume determination can be done using a variety of methods (e.g., using scattering and/or microscopy). In some embodiments, individual volumes of all of the droplets in the plurality may be determined. In some embodiments, only individual volumes of some of the droplets may be determined. Analyzing the droplets can also include determining the number of droplets that include a detectable agent (i.e., one or more detectable agents) further described herein. It is further noted that the second plurality of droplets is based on the same droplets produced as the first plurality of droplets. Thus, the first volume distribution can be the same or different (e.g., narrower) than the second volume distribution. If the distributions are the same, then each droplet in the first plurality will be included in the second plurality. In certain embodiments, the second volume distribution is narrower than the first volume distribution. For example, droplets can be produced in an emulsion having a volume distribution ranging from about 1 fL to about 100 nL. Depending, for example, on the concentration of the sample, analysis for digital measurements may be conducted for a volume distribution ranging from 1 fL to about 1 nL, in which the second volume distribution is narrower than the first volume distribution.

Reactions (e.g., amplification) can be carried out in volumes with different sizes, before or during analysis of the volumes to determine in which volumes have undergone reaction (e.g., have amplified product). In certain examples, the volumes (e.g., droplets) can be sized and the number of occupied droplets (e.g., droplets containing a detectable agent) counted. All or just some of the droplets can be analyzed. Analysis can, for example, be achieved by flowing the droplets in a single file through a flow cytometer or similar device, where the size of the droplet can be determined and the presence of amplification can be detected. The size of the droplet can, for example, determined based on the scattering signal from the droplet and the presence of amplification can be indicated by a fluorescence signal from the droplet. Alternatively, the diameter of droplets can be determined by microscopy. Droplets can be extracted (before, during, or after completion of a reaction, e.g., amplification) from a sample holder and imaged in widefield with a CCD camera. The droplets, e.g., can be spread out on a surface or embedded between two glass slides and placed under a widefield microscope. By using appropriate excitation and emission filters the fluorescence within the droplet can be quantified to reveal the presence or absence of amplification. By noting both the size of the droplet and the presence or absence of amplification product in each droplet, it is possible to back-calculate the original concentration of the analyte present in the sample after interrogating a sufficient number of droplets of different sizes. Because the droplets are of different sizes, for a given dynamic range, the analysis is much faster than if the droplets are all of similar size. In some embodiments, the methods herein further include using a number of droplets in a plurality and the individual volumes of the droplets in the plurality to conduct digital measurements. For example, a sample concentration of a molecule of interest can be determined using the number of droplets in the plurality, the number of droplets in the plurality with one or more molecules of interest, and by measuring the volume of some or all of the droplets in the plurality. Example methods for determining sample concentrations can be found in the Examples section.

The present invention can be used for any technique in which digital measurements provide useful information about a sample. As such, the methods, systems and devices provided herein can include a volume containing a detectable agent. In certain embodiments, the volume can be a well or chamber in a microfluidic chip or a droplet (e.g., a water droplet formed in an emulsion or on the surface of a chip) that contains the detectable agent. It will be generally understood that the detectable agent can include a single detectable molecule or a plurality of detectable molecules. Other types of detectable agents can be used, e.g., beads, quantum dots, nanoparticles, and the like. Furthermore, the detectable agent may, for example, be a molecule of interest present in a sample to be analyzed (e.g., a nucleic acid molecule in blood, serum, saliva or other solutions). Alternatively, a detectable agent can be a molecule that associates with a molecule of interest (e.g., the nucleic acid molecule) in the sample, thereby allowing the molecule to be detected. In some embodiments, the methods and systems of the present invention can be used for amplification-related techniques (e.g., digital PCR) involving digital measurements. For amplification measurements, a volume (e.g., a droplet) can include a single DNA molecule, for example, but the volume will also contain necessary components that are generally well known to be used for amplification and detection. In some embodiments, the detectable agent is fluorescent and, thus, can be detected by fluorescence-based detection methods known in the art. However, other detection methods (e.g., absorbance, chemiluminescence, turbidity, and/or scattering) can be used to analyze the contents of a volume. A variety of detectable agents suitable for the present invention are generally well known in the art and can, for example, be found in The Molecular Probes® Handbook, 11$^{th}$ Edition (2010).

In certain embodiments, the detectable agent can be associated with a molecule of interest for detection. For example, the detectable agent can be associated with a nucleic acid molecule (e.g., DNA or RNA), a peptide, a protein, a lipid, or other molecule (e.g., biomolecule) present in a sample. As defined herein, "associated" in the context of the detectable agent includes interaction with the molecule via covalent and/or non-covalent interactions. For example, the detectable agent can be covalently attached to the molecule of interest. Alternatively, the detectable agent can, for example, be an intercalation agent or a Taqman® probe that can be used to detect a nucleic acid molecule (e.g. a DNA and/or RNA molecule). Other detectable agents can be used, such as reference dyes that may not associate with molecules in a volume of interest.

Some embodiments of the present invention include producing droplets in immiscible fluids. As is well known in the art, a wide variety of immiscible fluids can be combined to produce droplets of varying volumes. As described further herein, the fluids can be combined through a variety of ways, such as by emulsification. For example, aqueous solution (e.g., water) can be combined with an non-aqueous fluid (e.g., oil) to produce droplets in a sample holder or on a microfluidic chip. Aqueous solutions suitable for use in the present invention can include a water-based solution that can further include buffers, salts, and other components generally known to be used in detection assays, such as PCR. Thus, aqueous solutions described herein can include, e.g., primers, nucleotides, and probes. Suitable non-aqueous fluids can include, but are not limited to, an organic phase fluid such as a mineral oil (e.g., light mineral oil), a silicone oil, a fluorinated oil or fluid (e.g., a fluorinated alcohol or Fluorinert), other commercially available materials (e.g., Tegosoft®), or a combination thereof.

In addition to aqueous solutions and non-aqueous fluids, surfactants can also be included to, e.g., improve stability of the droplets and/or to facilitate droplet formation. Suitable surfactants can include, but are not limited to, non-ionic surfactants, ionic surfactants, silicone-based surfactants, fluorinated surfactants or a combination thereof. Non-ionic surfactants can include, for example, sorbitan monostearate (Span 60), octylphenoxyethoxyethanol (Triton X-100), polyoxyethylenesorbitan monooleate (Tween 80) and sorbitan monooleate (Span 80). Silicone-based surfactants can include, for example, ABIL WE 09 surfactant. Other types of surfactants generally well known in the art can similarly be used. In some embodiments, the surfactant can be present at a variety of concentrations or ranges of concentrations, such as approximately 0.01%, 0.1%, 0.25%, 0.5%, 1%, 5%, or 10% by weight.

The present invention further includes determining a concentration of a sample. For example, the methods and systems can be used to determine (1) volumes of droplets and (2) a number of droplets that contain a detectable agent, which can be used to determine the concentration of a sample. This information can be used in a variety of ways to determine sample concentrations. For example, target molecules are present in the sample at a concentration in units of molecules/volume. The sample can be distributed into droplets of variable volumes that can be analyzed. The individual volumes of the droplets (all or just some) can be determined by methods provided herein. In addition, using detection methods described herein, droplets can be analyzed for containing a detectable agent or not. For a given sample concentration, some of the variable volume droplets may contain a detectable agent and some may not. For higher sample concentrations, generally more droplets of a plurality may contain detectable agents and vice versa; for low sample concentrations, fewer droplets of a plurality may be occupied by a detectable agent. As further described herein, the probabilities of occupancy by a detectable agent in a particular volume distribution can be defined for a wide range of sample concentrations, which can then be compared to real data to determine the concentration of an unknown sample. Additional disclosure for determining sample concentrations can be found in Examples 1 and 2 below. The method illustrated in the examples involves making an initial estimate for the sample concentration and then calculating the number of droplets, which would be predicted to contain one or more detectable agents (occupied droplets). The estimate for the sample concentration is then adjusted using a well-known numerical method until the predicted number of occupied droplets equals the actual number of occupied droplets in the plurality to within the desired degree of accuracy.

As further described herein, the present invention provides various aspects for digital measurements that cannot be achieved by some existing methods and systems. For example, the present invention can provide the ability to measure sample concentration over a wide dynamic range. In some embodiments, the dynamic range can be at least three orders of magnitude, at least four orders of magnitude, at least five orders of magnitude, or at least six orders of magnitude. In some embodiments, the dynamic range can be between about $10^{-1}$ to about $10^{-9}$ molecules/fL, about $10^{0.2}$ to about $10^{-8}$ molecules/fL, about $10^{-3}$ to about $10^{-7}$ molecules/fL, or about $10^{4}$ to about $10^{-6}$ molecules/fL. In certain embodiments, determining sample concentration within a dynamic range can be performed by detecting a detectable agent that is associated with a molecule of interest in the sample. Dynamic range can be dependent on a variety of factors, such as the range of volumes that are produced in an emulsion and/or the range of volumes that are analyzed and detected. For example, a first plurality of droplets having a first volume distribution can produce a dynamic range of detectable concentrations. In some instances, the dynamic range may be decreased by analyzing a narrower volume distribution in a second plurality of droplets having a second volume distribution. In certain embodiments, the volume distributions include continuously varying droplet volumes.

By integrating dPCR with on-chip gradient generation, or by using digitized volumes of varying sizes, or the combination of both these methods, the invention effectively increases the dynamic range of our dPCR chip from 1 order to 6 orders magnitude, which is comparable to the dynamic range offered by RT-PCR. By using a greater range of concentration gradients or arrays of digitized volumes with larger size differences, the dynamic range can be increased even further if desired. This new method for carrying out quantitative PCR (qPCR) offers several key advantages: (1) It is more accurate as discussed previously, (2) It obviates the need for running the type of calibration samples that is needed for RT-PCR and thus saves time, and (3) It removes the need for real-time sensitive fluorescence detection, which is responsible for the relatively higher cost (~10×) of RT-PCR versus regular PCR machines.

Another aspect of the invention comprises a device for carrying out the methods of the invention. Such devices may create arrays of digitized and discrete volumes of different sizes. In another embodiment, the device carries out the method for increasing the dynamic range of digital measurements of a sample, comprising creating a sample concentration gradient and creating sample volumes of different sizes.

In yet another aspect of the present invention, the methods, systems and devices described herein can be applied to isothermal amplification techniques, such as digital ELISA, NASBA, and LAMP. ELISA is protein based and usually used for the quantification of proteins or small molecules. NASBA and LAMP are isothermal amplification schemes that have been developed to complement PCR.

In an isothermal amplification, there is no temperature cycling occurring as in traditional PCR. There are several types of isothermal nucleic acid amplification methods such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification.

NASBA (Nucleic Acid Sequence Based Amplification) is an isothermal (~40° C.) process for amplifying RNA, and has been used successfully at detecting both viral and bacterial RNA in clinical samples. The advantages offered by NASBA are: (1) It has high amplification efficiency and fast amplification kinetics, where over thousand fold amplification can be achieved within an hour or two; (2) It does not give false positives caused by genomic dsDNA, as in the case of RT-PCR; (3) Gene expression studies can be performed without the use of intron flanking primers; (4) It does not require the degree of temperature control and feedback needed for PCR. As a result, NASBA has become popular for detecting viral and bacterial RNA. The fact that NASBA is an isothermal method makes it possible to run multiple samples simultaneously with the use of a temperature controlled oven, which is an important practical advantage in many field works.

LAMP, which stands for Loop-Mediated Isothermal Amplification, is capable of amplifying DNA with high specificity, efficiency, and rapidity under isothermal conditions (~60° C.). Because of the characteristics of its amplification reaction, LAMP is able to discriminate single nucleotide differences during amplification. As a result, LAMP has been applied for SNP (single nucleotide polymorphism) typing. LAMP has also been shown to have about 10 fold higher sensitivity then RT-PCR in the detection of viruses. Additionally, because LAMP amplification of DNA can be directly correlated with the production of magnesium pyrophosphate, which increases the turbidity of solution, the progress of LAMP has been monitored using a simple turbidimeter. Therefore, a non-homogenous assay can be used for detecting the amplification products that result from LAMP.

In one aspect, the present invention provides a method for performing digital loop-mediated amplification of a sample. The method can include producing a plurality of droplets of the sample on a microfluidic device, wherein at least one droplet in the plurality comprises a nucleic acid molecule (e.g., a DNA and/or a RNA molecule); and performing loop-mediated amplification in the at least one droplet to produce amplified product of the nucleic acid molecule. The method can also include detecting the amplified product. In some embodiments, the method includes determining a number of droplets in the plurality that comprise the amplified product; and calculating a concentration of the nucleic acid molecule in the sample using individual volumes of the droplets in the plurality and the number of droplets in the plurality that contain the nucleic acid molecule. The microfluidic device can include a plurality of chambers configured to form the plurality of droplets. Additional aspects of performing digital LAMP with the present invention can be found in Example 3.

Despite some of the advantages offered by NASBA and LAMP, one important drawback is the difficulty with performing quantification, which would be beneficial in most situations. Quantification often requires meticulous calibration and control using standards amplified under identical conditions, which can be very tedious (especially for field studies) and is not practical in many cases. For non-homogenous assays, such as the detection of precipitate in LAMP, accurate calibration can be especially challenging.

Rolling circle amplification (RCA) is an isothermal nucleic-acid amplification method. It differs from the polymerase chain reaction and other nucleic-acid amplification schemes in several respects. During RCA, a short DNA probe anneals to a target DNA of interest, such as the DNA of a pathogenic organism or a human gene containing a deleterious mutation. The probe then acts as a primer for a Rolling Circle Amplification reaction. The free end of the probe anneals to a small circular DNA template. A DNA polymerase is added to extend the primer. The DNA polymerase extends the primer continuously around the circular DNA template generating a long DNA product that consists of many repeated copies of the circle. By the end of the reaction, the polymerase generates many thousands of copies of the circular template, with the chain of copies tethered to the original target DNA. This allows for spatial resolution of target and rapid amplification of the signal. The use of forward and reverse primers can change the above linear amplification reaction into an exponential mode that can generate up to 1012 copies in 1 hour. The calibration required for such quantitative measurements can be cumbersome.

To overcome this drawback, the present invention provides digital isothermal amplifications, such as NASBA and LAMP, where the use of an array of digitized volumes, similar to digital PCR, is used for carrying out digital NASBA, digital LAMP, and rolling circle amplification. Furthermore, by using concentration gradients and/or arrays of digitized volumes of different sizes, we can effectively increase the dynamic range of these digital measurements. The current method ideally complements these isothermal amplification schemes to make them a quantitative technique for measuring the presence of RNA and DNA. In another embodiment of the invention, the method is applied to antibody based amplification. In another embodiment, the method is applied to specific molecule recognition based amplification.

III. Systems for Digital Measurements

In yet another aspect, the present invention provides systems for using digital measurements to determine a concentration of a sample. The systems can include a sample holder containing a first plurality of droplets having a first volume distribution; a detector for detecting a detectable agent contained in at least one droplet of the first plurality; and a computer comprising a memory device with executable instructions stored thereon, the instructions, when executed by a processor, cause the processor to: analyze a second plurality of droplets having a second volume distribution to determine volumes of the droplets in the second plurality and a number of droplets in the second plurality that contain a detectable agent, wherein the first volume distribution is the same or different than the second volume distribution; and use volumes of the droplets in the second plurality and the number of droplets in the second plurality that contain the detectable agent to determine the concentration of the sample. In some embodiments, the concentration of the detectable agent in the sample is used to calculate the sample concentration.

As described further herein, the volumes used for digital measurements can be generated and analyzed by a variety of ways. The present invention includes a sample holder that can be used to hold the volumes so that the volumes can be further processed and/or analyzed. The sample holders of the present invention can include test tubes, eppendorf tubes, arrays of wells on a microarray or in a microfluidic chip, a microfluidic chip configured to generate droplets, as well as other commercially available or otherwise generally known devices capable of holding discrete volumes (e.g., wells or droplets) of a sample. The systems of the present invention further include a detection system configured to analyze the volumes. The detection systems can include detectors for analyzing the contents of the volumes, determining volumes of droplets, and/or other characteristics of interest. The methods described herein will be generally compatible with any known systems capable of detecting and analyzing volumes (e.g., droplets and/or wells).

In yet another aspect, the systems can include a computer-readable storage medium for conducting digital measurements. The computer-readable storage medium has stored thereon instructions that, when executed by one or more processors of a computer, cause the computer to: analyze a second plurality of droplets having a second volume distribution to determine a number of droplets in the second plurality that contain the detectable agent, wherein the first plurality of droplets comprises the second plurality of droplets and the second volume distribution is narrower than the first volume distribution; and use the number of droplets in the second plurality, the volumes of some or all of the droplets in the second plurality and the number of droplets in the second plurality containing one or more detectable agents to determine a concentration of the detectable agent in the sample.

In yet another aspect, a system is provided for analyzing volumes to detect and calculate information from the analyzed volumes. The system includes one or more processors, and a memory device including instructions executable by the one or more processors. When the instructions are executed by the one or more processors, the system at least receives a user input to analyze volumes (e.g., a plurality of droplets). The system can be configured to carry out aspects of the methods of the present invention, such as counting a number of volumes (e.g., droplets), determining volumes of a plurality of droplets in a volume distribution and use the number of the droplets containing one or more detectable agents to determine a concentration of the detectable agent in the sample. The system also provides data to a user. The data provided to the user can include the concentration of the detectable agent in the sample or a sample concentration.

Figure 3:
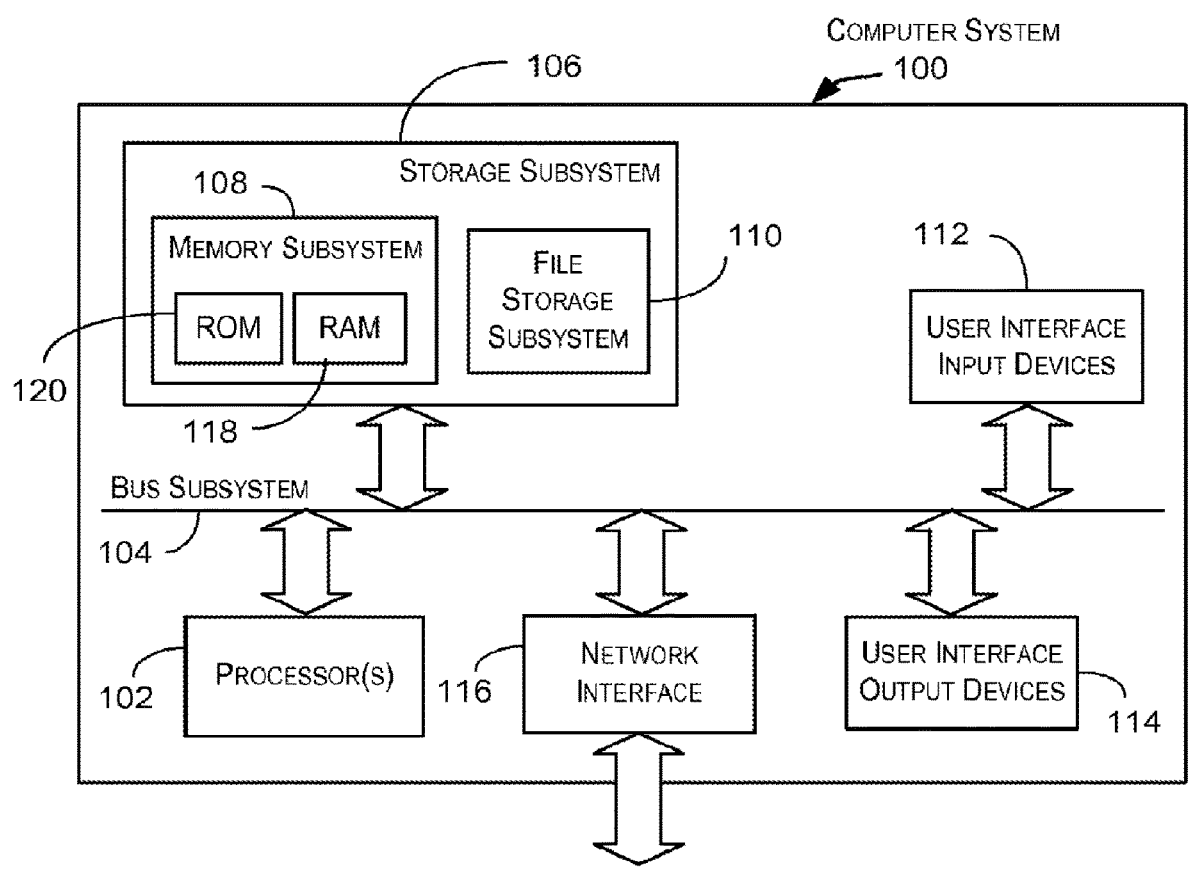
FIG. 3 provides an illustration of a computer system, in accordance with an embodiment of the present invention.

FIG. 3 is a simplified block diagram of a computer system 100 that may be used for the methods, media and systems described herein. In various embodiments, computer system 100 may be used to implement any of the systems or methods illustrated and described above. As shown in FIG. 3, computer system 100 includes a processor 102 that communicates with a number of peripheral subsystems via a bus subsystem 104. These peripheral subsystems may include a storage subsystem 106, comprising a memory subsystem 108 and a file storage subsystem 110, user interface input devices 112, user interface output devices 114, and a network interface subsystem 116.

Bus subsystem 104 provides a mechanism for enabling the various components and subsystems of computer system 100 to communicate with each other as intended. Although bus subsystem 104 is shown schematically as a single bus, alternative embodiments of the bus subsystem may utilize multiple busses.

Network interface subsystem 116 provides an interface to other computer systems and networks. Network interface subsystem 116 serves as an interface for receiving data from and transmitting data to other systems from computer system 100. For example, network interface subsystem 116 may enable a user computer to connect to the Internet and facilitate communications using the Internet.

User interface input devices 112 may include a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to computer system 100.

User interface output devices 114 may include a display subsystem, a printer, a fax machine, or non-visual displays such as audio output devices, etc. The display subsystem may be a cathode ray tube (CRT), a flat-panel device such as a liquid crystal display (LCD), or a projection device. In general, use of the term "output device" is intended to include all possible types of devices and mechanisms for outputting information from computer system 100. An advertisement may be output by computer system 100 using one or more of user interface output devices 114.

Storage subsystem 106 provides a computer-readable storage medium for storing the basic programming and data constructs. Software (programs, code modules, instructions)

that when executed by a processor provide the functionality of the methods and systems described herein may be stored in storage subsystem 106. These software modules or instructions may be executed by processor(s) 102. Storage subsystem 106 may also provide a repository for storing data used in accordance with the present invention. Storage subsystem 106 may include memory subsystem 108 and file/disk storage subsystem 110.

Memory subsystem 108 may include a number of memories including a main random access memory (RAM) 118 for storage of instructions and data during program execution and a read only memory (ROM) 120 in which fixed instructions are stored. File storage subsystem 110 provides a non-transitory persistent (non-volatile) storage for program and data files, and may include a hard disk drive, a floppy disk drive along with associated removable media, a Compact Disk Read Only Memory (CD-ROM) drive, an optical drive, removable media cartridges, and other like storage media.

Computer system 100 can be of various types including a personal computer, a portable computer, a workstation, a network computer, a mainframe, a kiosk, a server or any other data processing system. Due to the ever-changing nature of computers and networks, the description of computer system 100 depicted in FIG. 3 is intended only as a specific example for purposes of illustrating the embodiment of the computer system. Many other configurations having more or fewer components than the system depicted in FIG. 3 are possible.

The specific dimensions of any of the apparatuses, devices, systems, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those expressly set forth. Accordingly, the present invention is intended to be described solely by reference to the appended claims, and not limited to the embodiments disclosed herein.

IV. Examples

Example 1

Example Theoretical Framework

This example describes a non-limiting theoretical framework that can be used to describe certain aspects of the present invention described herein. It will be understood that the method described in this example is one of many ways to determine concentrations of sample using the present invention. Under this theoretical framework, it is assumed that the target molecules are present in the sample at a concentration $C_S$ in units of molecules/volume. The sample is distributed into digital volumes of variable volumes; the distribution of target molecules into the droplets follows Poisson statistics. For each droplet in the digital array and as shown in Equation 1, the average number of targets depends on its volume $V_i$, and the initial sample concentration $C_S$:

$$P(n, C_S V_i) = \frac{(C_S V_i)^n}{n!} \exp(-C_S V_i) \quad (1)$$

is the probability of finding n molecules in a droplet of volume $V_i$ for a given concentration $C_S$ of target molecules in solution. The amplification reaction will cause a droplet containing one or more molecules to be distinguishable from empty droplets, e.g. by its fluorescence intensity. In this method we know only whether a droplet is empty or occupied. The associated probabilities are shown in Equation 2:

$$P(0, C_S V_i) = \exp(-C_S V_i)$$

$$P(n>0, C_S V_i) = 1 - \exp(-C_S V_i) \quad (2)$$

In order to determine the concentration $C_S$ of target molecules, $P(n>0, C_S V_i)$ needs to be summed over a sufficiently large number of droplets with respective volumes $V_i$.

Simulation Methods

Simulations of a digital amplification assay are described, e.g. digital PCR, digital LAMP or digital ELISA, with continuous variable volumes to validate, that the target concentration $C_S$ can be accurately determined.

For each simulation a fixed number of droplets, $N_d$, and simulated concentration of analyte molecules, $C_S$, was chosen. Simulations were performed for various values of $C_S$. A random number generator was used to choose the diameters for $N_d$ droplets from a given range and distribution. To illustrate the principle of this invention, simulations were performed assuming that the droplet diameter D is uniformly distributed between a minimum diameter of 4 microns and a maximum diameter of 190 microns. This results in simulated volumes which range from 34 to $3.6 \times 10^6$ fL. A more realistic distribution of droplet diameters is discussed below.

In each simulation a random number generator is used to determine whether a particular simulated droplet is occupied or empty, when the initial target concentration is $C_S$. The total number of occupied droplets in a simulation, $N_s$, is counted and subsequently compared to the expected number of occupied droplets $$N_E = \sum_{i=1}^{N_d} (1 - \exp(-CV_i)) \quad (3)$$

where the most probable value of $N_E$ is obtained for $C=C_S$. Using the volumes of the $N_d$ droplets, equation (3) can be fit to $N_s$ to obtain a best fit value of the concentration, with C being the only adjustable parameter. We use the Newton-Rhapson algorithm to find the zero of $N_s - N_E$. The initial value of C is obtained by replacing the $V_i$'s in equation (3) with the median volume of the distribution and solving for C. The algorithm then typically takes 5-11 iterations for the changes in C to fall below 1 part in $10^5$. The value of C at that point is taken to be the best fit value of C.

For the simulations, some of the goals are (i) to determine how accurately this procedure is in estimating $C_S$ and (ii) if two different samples yield different best fit values of C, how to calculate the confidence that the samples have different concentrations.

This method includes the measurement of the volume of each droplet, and there can be an error associated with that which is taken into account. To simulate this, a Gaussian distributed error is added to each of the simulated diameter to yield simulated measured diameters. These simulated measured diameters are then used to calculate simulated measured volumes, $\hat{V}_i$ which are substituted into equation (3) to yield the expected number of occupied droplets based on measured volumes.

$$\hat{N}_E = \sum_{i=1}^{N_d} \left(1 - \exp(-C\hat{V}_i)\right) \quad (4)$$

One method for determining the droplet diameters is by microscopy. The accuracy of this method can depend on the numerical aperture (NA) of the objective used as well as other details of the imaging system. For imaging a large number of stationary droplets on a surface the NA would likely be less than 1 and in our experience the errors in the diameter measurements is typically 0.5 to 1.0 microns independent of the size of the droplet. We simulated two different magnitudes of measurement error, denoted $E_1$ and $E_2$. For $E_1$ the standard deviation of the Gaussian distributed error added to a droplet diameter is the larger of 1 micron or 8% of that droplet's diameter. The relative error is included so that the simulation includes a non-negligible measurement error for the largest droplets. For $E_2$ the standard deviation of the Gaussian distributed error added to a droplet diameter is the larger of 2 micron or 15% of that droplet's diameter. In both cases there is one limit placed on the simulated measured diameters. If a particular Gaussian deviate results in a droplet diameter being less than 0.5 microns, then that deviate is discarded and a new one generated for that droplet.

In the analysis of an experiment $C_S$ is the actual, unknown concentration which the procedure is attempting to determine, C is the best fit estimate, the $V_i$'s are actual volumes of the droplets and the $\hat{V}_i$'s are the volumes measured by the experimenter.

Simulation Results

Figure 4:
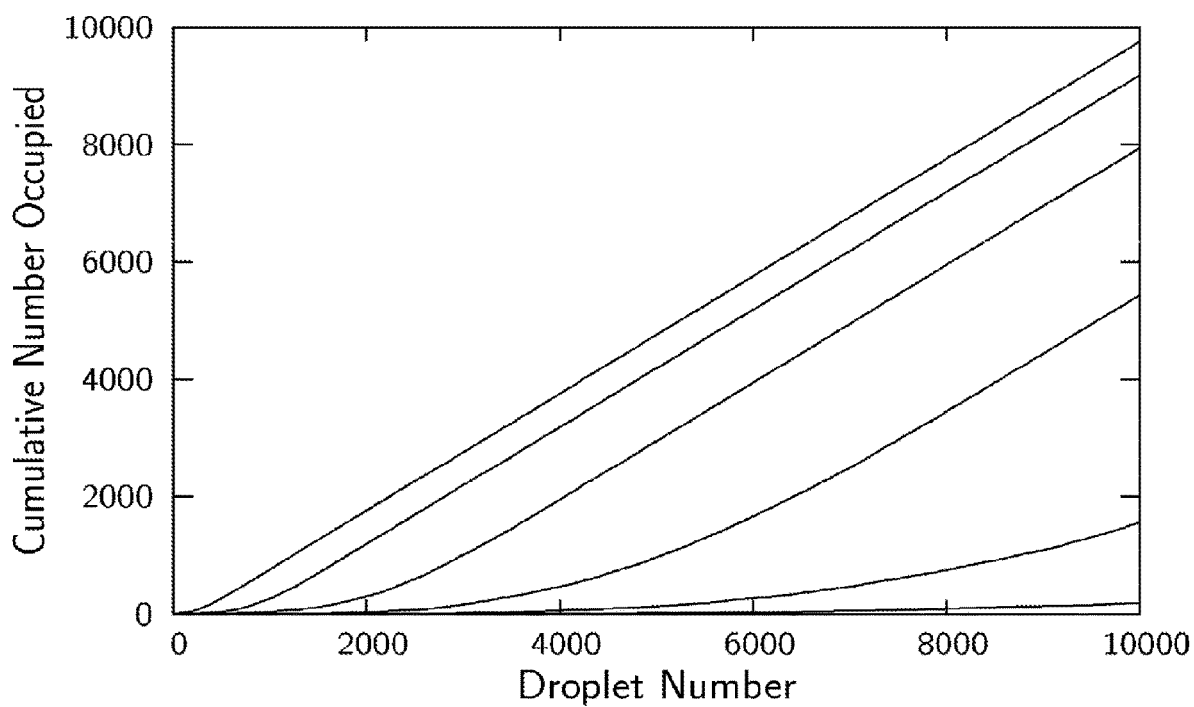
FIG. 4 depicts a relationship of a cumulative number of occupied droplets versus droplet number, in accordance with an example embodiment of the present invention. The size simulations are for concentrations (from left to right in the plot) $2.0 \times 10^{-3}$, $2.0 \times 10^{-4}$, $2.0 \times 10^{-5}$, $2.0 \times 10^{-6}$, $2.0 \times 10^{-7}$, and $2.0 \times 10^{-8}$ molecules/fL. All simulations contained 10,000 droplets whose diameters were drawn from a uniform distribution extending from 4 to 190 microns. All droplets were sorted by volume from smallest to largest and the cumulative number of occupied droplets for droplet number i was the total number of occupied droplets with droplet numbers $\leq i$.

Results for a typical set of simulations are shown in FIG. 4. Simulations were performed with 10,000 droplets and six different concentrations $C_S$ ($2.0\times10^{-3}$, $2.0\times10^{-4}$, $2.0\times10^{-5}$, $2.0\times10^{-6}$, $2.0\times10^{-7}$, and $2.0\times10^{-8}$ molec/fL). The droplet sizes were drawn from a uniform distribution of diameters between 4.0 and 190 microns. For each simulation, the droplets were sorted by volume, the droplet with the smallest volume was number 1 and the droplet with the largest volume was number 10,000. FIG. 4 plots the cumulative number of occupied droplets. The cumulative number occupied for the ith droplet is the sum of the occupied droplets for all droplets ≤i.

The shape of the curve is a function of both the concentration and the shape of the distribution of droplet volumes. A distribution which is uniform in droplet volume (instead of droplet diameter) would yield different shaped curves, as would non-uniform distributions. For any given distribution of sizes, curves of the type in FIG. 4 will rise monotonically with droplet number, and curves for different concentrations will never cross. So once the distribution of droplet sizes has been measured, the shape of the curve and the total number of occupied droplets depends only on the concentration of analyte molecules. For sufficiently large concentrations, there is a droplet volume where the probability of being occupied is very close to 1.0. Once the droplet number corresponding to that volume has been reached, the curve rises with near unit slope for all larger droplet numbers. For sufficiently small concentrations there is a droplet volume below which the probability of being occupied is indistinguishable from 0.0. For all droplet numbers smaller than the droplet number corresponding to that volume the curves equal zero.

Effect of Measurement Error of the Droplet Diameters on Best Fit Results

As described herein, the present invention involves individually measuring sizes of droplets. Since the volume of a droplet enters into the probability of it being occupied, it would appear that it is important that the volumes be measured very accurately. For the range of droplet sizes in this simulation, the smallest droplets (≈4 micron diameter) are not substantially larger than typical errors in measuring droplet diameters by light microscopy (≈1 micron standard deviation). The resulting relative errors in the droplet volume can be significant and might be expected to degrade the accuracy of this method. Surprisingly, this does not appear to be the case. Table 1 compares the results of fitting equation (3) with the results of fitting equation (4) to a series of simulations. For each concentration, 100 simulations were performed, each containing 2000 droplets. For equation (3) the simulated volumes, $V_i$, were used. For equation (4), simulated measured volumes, $\hat{V}_i$, were used. The point is that the results of fitting the simulated results using equation (3) represents the best fit concentrations that are obtained when the volumes of the droplets are known with perfect accuracy, while the results of fitting with equation (4) includes the effect of errors in the measurement of the droplet volumes. The average and standard deviations for the best fit concentrations using equations (3) and (4) are listed in Table 1 for both $E_1$ and $E_2$.

TABLE 1

Effects of volume measurement errors in simulations of 2000 droplets

| Simulation | Best fit using V | | Best fit using $\hat{V}$ | |
| --- | --- | --- | --- | --- |
| $C_S$ | C | $\sigma_C$ | C | $\sigma_C$ |
| $E_1$ (±1.0 micron or 8% error(a)) | | | | |
| $8.00 \times 10^{-9}$ | $7.80 \times 10^{-9}$ | $2.04 \times 10^{-9}$ | $7.66 \times 10^{-9}$ | $2.01 \times 10^{-9}$ |
| $8.00 \times 10^{-8}$ | $7.97 \times 10^{-8}$ | $6.78 \times 10^{-9}$ | $7.85 \times 10^{-8}$ | $6.73 \times 10^{-9}$ |
| $8.00 \times 10^{-7}$ | $8.02 \times 10^{-7}$ | $3.38 \times 10^{-8}$ | $8.10 \times 10^{-7}$ | $3.52 \times 10^{-8}$ |
| $8.00 \times 10^{-6}$ | $8.01 \times 10^{-6}$ | $4.45 \times 10^{-7}$ | $8.17 \times 10^{-6}$ | $4.59 \times 10^{-7}$ |
| $8.00 \times 10^{-5}$ | $8.06 \times 10^{-5}$ | $6.98 \times 10^{-6}$ | $8.22 \times 10^{-5}$ | $7.17 \times 10^{-6}$ |
| $8.00 \times 10^{-4}$ | $8.11 \times 10^{-4}$ | $9.64 \times 10^{-5}$ | $8.23 \times 10^{-4}$ | $1.00 \times 10^{-4}$ |
| $8.00 \times 10^{-3}$ | $8.19 \times 10^{-3}$ | $1.55 \times 10^{-3}$ | $8.66 \times 10^{-3}$ | $1.84 \times 10^{-3}$ |
| $E_2$ (±2.0 micron or 15% error(a)) | | | | |
| $8.00 \times 10^{-9}$ | $8.03 \times 10^{-9}$ | $2.13 \times 10^{-9}$ | $7.53 \times 10^{-9}$ | $2.01 \times 10^{-9}$ |
| $8.00 \times 10^{-8}$ | $8.00 \times 10^{-8}$ | $6.89 \times 10^{-9}$ | $7.61 \times 10^{-8}$ | $6.76 \times 10^{-9}$ |
| $8.00 \times 10^{-7}$ | $8.02 \times 10^{-7}$ | $3.35 \times 10^{-8}$ | $8.30 \times 10^{-7}$ | $3.77 \times 10^{-8}$ |
| $8.00 \times 10^{-6}$ | $8.00 \times 10^{-6}$ | $4.57 \times 10^{-7}$ | $8.60 \times 10^{-6}$ | $5.13 \times 10^{-7}$ |
| $8.00 \times 10^{-5}$ | $8.04 \times 10^{-5}$ | $6.76 \times 10^{-6}$ | $8.62 \times 10^{-5}$ | $7.46 \times 10^{-6}$ |
| $8.00 \times 10^{-4}$ | $8.10 \times 10^{-4}$ | $1.06 \times 10^{-4}$ | $8.52 \times 10^{-4}$ | $1.16 \times 10^{-4}$ |
| $8.00 \times 10^{-3}$ | $8.15 \times 10^{-3}$ | $1.51 \times 10^{-3}$ | $1.01 \times 10^{-2}$ | $2.93 \times 10^{-3}$ |

(a)The larger of the fixed and relative errors for each droplet is used as the standard deviation of the Gaussian distributed error added to that droplet to generated simulated measured diameters from the simulated diameters. These are used to calculate the simulated measured volumes ($\hat{V}$) and simulated volumes (V), respectively.

The differences between the best fit concentrations using equations (3) and (4) are very small except the very largest concentrations. Even when the error is ±2 microns or 15%, the error only reaches 25% for the largest concentration. Furthermore, for each concentration, the standard deviations of the best fit results using equations (3) and (4) are, except for the largest concentration, nearly the same, without any apparent systematic difference between them. This suggests that for most of the concentrations in Table 1 that the largest source of variability in the best fit concentrations is the variation in the droplet occupancy numbers from one simulation to the next. Any variability in the best fit results due to the droplet size measurement errors has a small or negligible effect on the concentration determination so long as it is unbiased. All of this is despite the fact that for the smallest droplets one standard deviation of the error is close to half the diameter for the simulations with 2.0 micron error ($E_2$). This is an important result since it means that this method does not require that an unreasonably high accuracy in the measurement of the droplet diameters. As is discussed below it primarily requires that any measurement error be unbiased. This surprising result can be explained with the help of FIG. 5.

Figure 5:
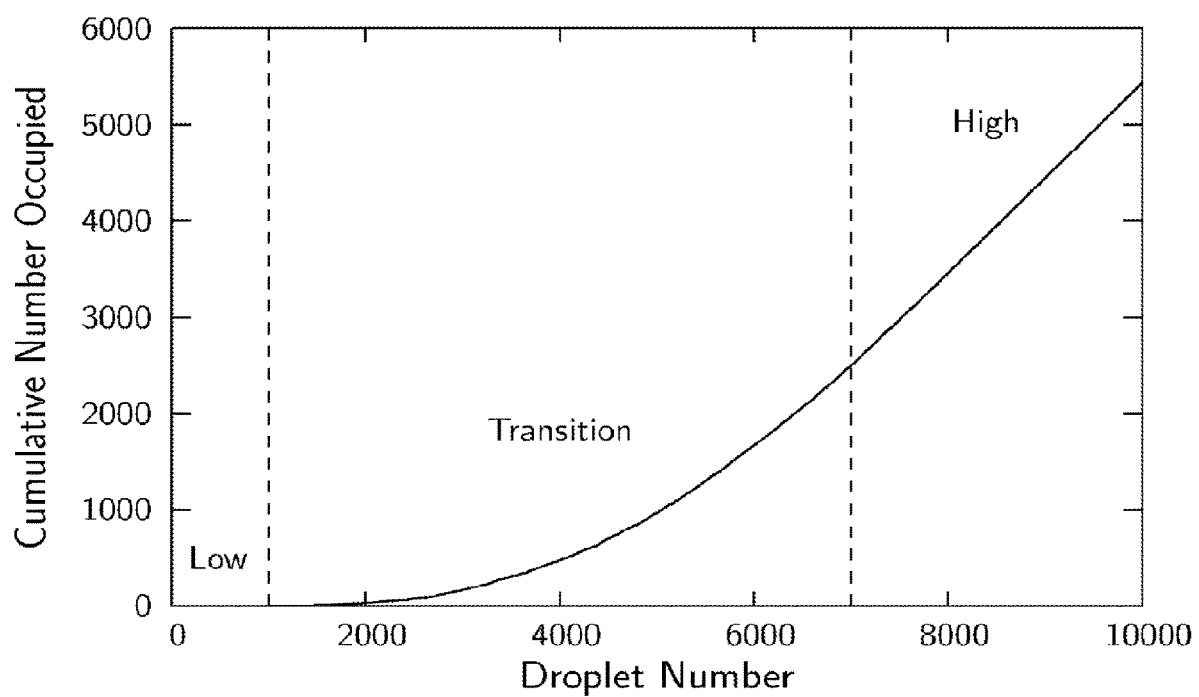
FIG. 5 provides a simulation of cumulative number of occupied droplets for a concentration of $2.0 \times 10^{-6}$ and in accordance with an example embodiment of the present invention. Other details are the same as in FIG. 1. In the Low region, the probability of a droplet being occupied is very small and so the simulated curve is zero there. In the High region, the probability of a droplet being occupied is very close to 1 and the curve rises with near unit slope there. In the Transition region, the probability of a droplet being occupied increases from near zero to almost 1.

FIG. 5 shows the results of a simulation of the cumulative number of occupied droplets for a concentration of $2.0 \times 10^{-6}$. The simulation includes 10,000 droplets whose diameters are uniformly distributed between 4 and 190 microns. The curve is divided into three regions: Low, Transition and High. In the Low region, the probability of a droplet being occupied is very small and so the simulated curve is zero there. In the High region, the probability of a droplet being occupied is very close to 1 and the curve rises with near unit slope there. In the Transition region the probability of a droplet being occupied increases from near zero to almost 1. Measurement errors for droplets within the Low or High regions will have little or no effect on the total number of occupied droplets. From equation (4) we see that a measurement error on a droplet within the Low region simply replaces a term in the sum which is nearly zero with a different term which is also nearly zero which should result in a negligible change in the total number of occupied droplets. A similar effect occurs in the High region where measurement errors replace terms in equation (4) which are nearly 1.0 with other terms which are also nearly 1.0. If the errors are unbiased, as they are in the simulations in Table 1, then there will also be some cancelation of the errors. The terms in sum in equation (4) which correspond to droplets in either the Low or High region are as likely to be replaced by a slightly larger term as they are to be replaced by a slightly smaller term. Therefore, there will be some cancelation of the droplet volume measurement errors which will reduce the effect of those errors on the best fit concentration. If the errors are unbiased and if there are enough droplets distributed throughout the volumes which define the Transition region, then some cancelation of the volume measurement errors for droplets within the Transition region also appears to occur. In fact it seems that volume measurement errors will introduce significant errors in the best fit concentrations only when the measurement errors significantly change the shape of the distribution function of the volumes, and even then only if the change occurs for those droplets within the Transition region. The effect of the Gaussian distributed measurement errors used in Table 1 on the distribution of diameters is only noticeable near the ends of the distribution. For example, the smallest droplets generated in these simulations have diameters near 4 microns. However, when measurement error is included, the simulated measured diameters can be less than 4 microns. That is, the distribution of simulated measured diameters will extend to smaller sizes than the actual simulated diameters, which would be a slight broadening of the distribution function near 4 microns. For these smallest droplets, the probability of being occupied is calculated using the simulated size, but when fitting the data, the probability of being occupied is calculated using the smaller measured size. This can lead to the fit over estimating the concentration when the Transition region includes these smallest droplets. This is what is seen in Table 1, though the effect is not very large. There should be an equivalent effect at the lowest concentrations due to a slight broadening of the distribution function near 190 microns, but the effect is not as noticeable.

The range of droplet diameters used in these simulations was chosen so that any reasonable sized droplet volume measurement error might be expected to have a noticeable effect on attempts to estimate the concentration from the total number of occupied droplets. However, this does not appear to have occurred, even though the range of concentrations simulated ($10^6$) is larger than the range of volumes simulated ($10^5$). Other simulations with droplet diameters uniformly distributed over smaller ranges (10 and $10^3$) yield similar results in that reasonably accurate best fit concentrations can be obtained over a range of simulated concentrations larger than the range of volumes by approximately a factor of 10.

A different question arises if this method is used to determine if the concentrations of two different samples are different. For that the confidence and statistical power of this method must be consider. This is done in the next section.
Estimation of Confidence and Power The ability of a method to distinguish a difference in concentrations can be described in terms of confidence and power. (Lieber, R. L. (1990) "Statistical Significance and Statistical Power in Hypothesis Testing", J. Orthopaedic Research 8, 304-309) If measurements on two different samples yield two different best fit concentrations ($C_1$ and $C_2$), it would be useful to know how confident one could be in asserting that the concentrations of the two samples are different, and also the probability of being wrong if one concluded that they were not different. The risk of a false positive result (Type I error) is controlled by requiring that the results have a required minimum confidence and the risk of a false negative result (Type II error) is controlled by requiring that the method have a required power.

For the comparison of two best fit concentrations from two different samples, the null hypothesis would be that the two samples had the same (unknown) concentration. If $\alpha$ is the probability that two samples with the same concentration could result in best fit concentrations which differ in magnitude by more than $|C_1-C_2|$, then $(1-\alpha)$ is the confidence associated with rejecting the null hypothesis. The acceptable minimum value of $(1-\alpha)$ is chosen to limit false positive results. The use of the power to guard against false negatives is described later.

One method used to estimate confidence levels is the Z-test.

$$Z = \frac{C_1 - C_2}{\sqrt{\sigma_1^2 + \sigma_2^2}} \qquad (5)$$

A confidence level of 95% is a common choice and requires $Z > 1.96$. The $C_n$ are the best fit results of equation (4) and $\sigma_n^2$ is the variance associated with the measurement of $C_n$. A tractable analytical expression for the $\sigma_n^2$ does not appear to exist for our method, so it is necessary to estimate the $\sigma_n^2$ by simulation. Furthermore, one additional limitation of the Z test is that it assumes that the measurement results are normally distributed. Since this is not necessarily the case a second simulation method to estimate the confidence was performed and compared with the Z test results. Hereafter, the two methods will be denoted the Z method and Pairs or P method.

For the Z method estimate of the confidence, we used two different values of $C_S$ ($C_{S1}$=2.0×10$^{-5}$ and $C_{S2}$=2.2×10$^{-5}$). For each value of $C_S$ a set of 5000 droplets was randomly selected from a uniform distribution in droplet diameters extending from 4 to 190 microns and equation (2) was used to simulate the number of occupied droplets. The $E_1$ size of measurement errors was used to generate simulated measured volumes. Best fit values for each set were determined to obtain $C_1$ and $C_2$, where $C_n$, is the best fit result for the simulation which used $C_{Sn}$ for its simulated concentration. For each $C_n$, additional Z method simulations were performed. $C_n$ and the simulated measured volumes, $\hat{V}_i$, were used in equation (2) to obtain $N_Z$=1000 additional, simulated total number of occupied droplets for the set of $\hat{V}_i$. These are then fit using equation (2) to obtain $N_Z$ best fit concentrations, $C_n^Z$. The standard deviation of the $C_n^Z$ is used for $\sigma_n$ in equation (5). This corresponds to the information an experimenter would have. An estimate of the confidence could be calculated from the best fit concentrations, $C_n$, and the measured droplet volumes $\hat{V}_i$.

For the Pairs method estimate of the confidence we assume that the null hypothesis is that the two best fit results ($C_1$ and $C_2$) were each obtained from a sample whose actual concentration, $\overline{C}$, is the average of the two best fit concentrations. $N_p$=500 additional sets of droplet diameters were simulated and for each, the number of occupied droplets were simulated for the concentration $\overline{C}$, and the $E_1$ size of measurement errors was used to generate simulated measured volumes. A best fit concentration $\overline{C}'$ was obtained for each set. Then $M_p$=500 pairs of values were randomly selected with replacement from the set of $\overline{C}'$ and the absolute value of their differences ($\delta \overline{C}'_p$, p=1, K, $M_p$) were compared with $\Delta C = C_2 - C_1$. The fraction of the $\delta \overline{C}'_p$ which are greater than $\Delta C$ provides an estimate of $\alpha$, the probability that two measurements made from a sample with concentration $\overline{C}$ would differ from each other by more than $\Delta C$. The P method estimate of $\alpha$ is used to calculate the confidence, which equals (1-$\alpha$).

The entire procedure for obtaining two estimates of the confidence was repeated for pair of $C_S$ values 100 times. For each repetition, a new set of simulated volumes was generated for each $C_S$ and equation (2) was used to generate the number of occupied droplets for each $C_S$. Simulated measured volumes were generated and used in equation (4) to fit the results and obtain a new pair of best fit concentrations ($C_1$ and $C_2$. The Z method and P methods were then used to estimate the confidence.

The small difference between the two chosen values of $C_S$ (10%) results in confidences which range from near zero to near 1. This permits us to compare the two methods of estimating the confidence over a range of values, and reasonable agreement was obtained in all cases. Table 2 in FIG. 17 shows a few of the 100 results. In particular, Table 2 shows the 5 sets which resulted in the smallest values of the confidence, 6 sets which resulted in confidence values at the median, and 5 sets which resulted in the confidence values near 1.0. The results from the Z method are shown in the first 5 columns and the results from the P method are shown in the last 3 columns. The values of the confidence, (1-$\alpha$), for the two different methods are in columns 5 and 8 and reasonable agreement between them is found for all of the sets simulated. The absence of an analytical expression does not pose a problem as, the Z test as implemented in the Z method appears to be sufficiently accurate. While we continue to use the P method in the calculation of the power, in practice the Z method is a reasonable alternative and is computationally less expensive. Furthermore, the P method requires a numerical method for generating distributions of the droplet sizes which is a good approximation to the actual distribution, while the Z method does not. This last requirement is not a problem in simulations, but could be a difficulty in analyzing experimental results, so the Z method would be more useful in that case. We note that the Z method, which uses the same experimentally measured droplet sizes for all of its $N_Z$ simulations, produces confidences which are in reasonable agreement with those of the P method, which generates a new set of simulated droplet volumes and associated measurement errors for each of its $N_P$ simulations. This implies that for a sufficiently large number of droplets, the variation in a particular sample's distribution of droplet volumes is a less significant contributor to the variability in the number of occupied droplets than Poisson probability of a droplet being occupied (equation (2)).

Figure 6:
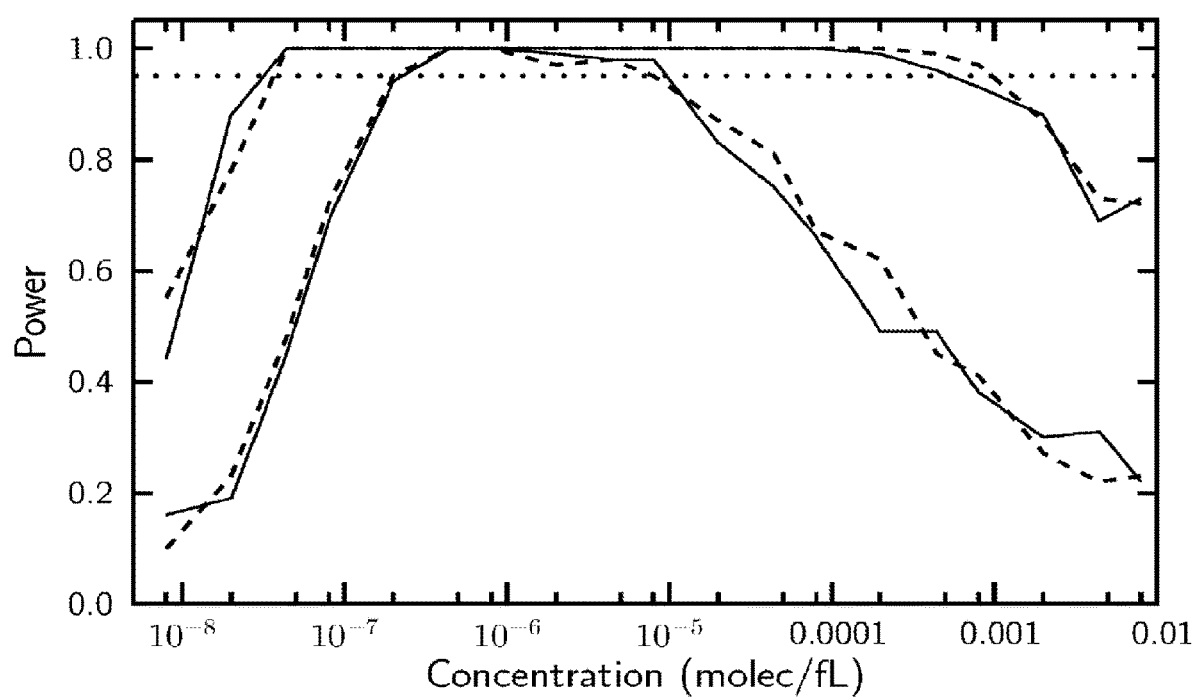
FIG. 6 shows estimated power for a uniform droplet distribution (4 to 190 micron diameter), in accordance with an example embodiment of the present invention. The dashed lines are for measurement errors of size $E_1$ and the solid lines are for measurement errors of size $E_2$. The lower two lines are for a 1.2 fold resolution, and the upper two lines are for a 1.5 fold resolution. The dotted line is drawn at 0.95.
Figure 7:
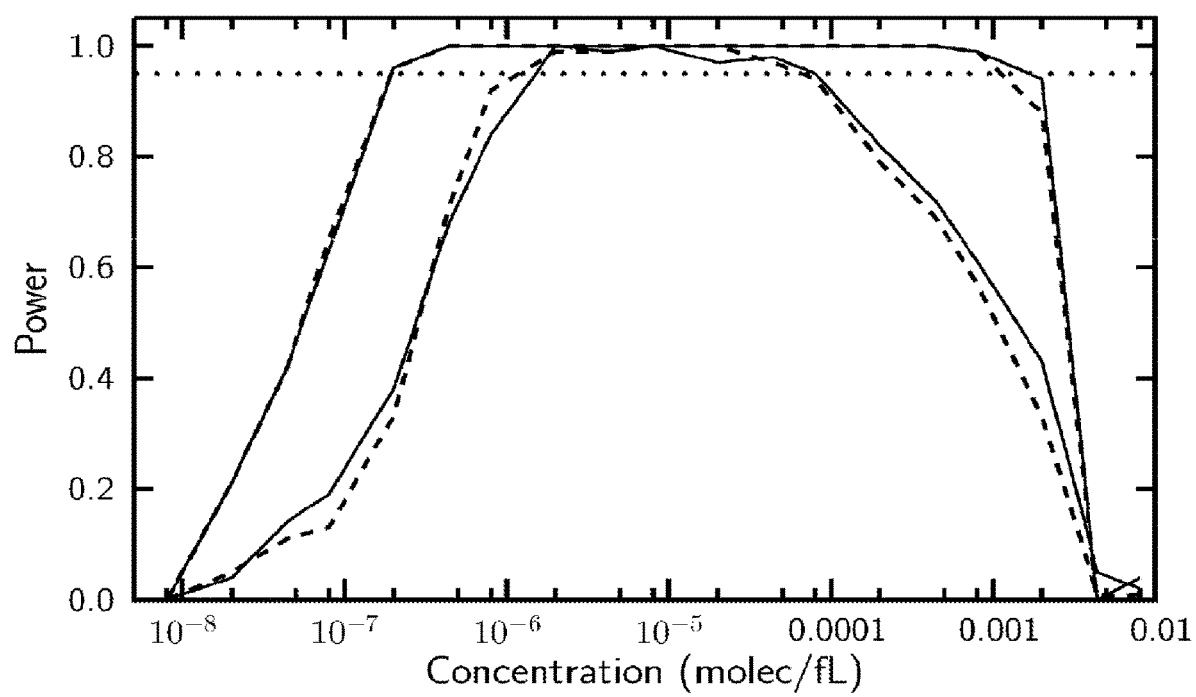
FIG. 7 shows estimated power for uniform droplet distribution (10 to 100 micron diameter), in accordance with an example embodiment of the present invention. The dashed lines are for measurement errors of size $E_1$ and the solid lines are for measurement errors of size $E_2$. The lower two lines are for a 1.2 fold resolution, and the upper two lines are for a 1.5 fold resolution. The dotted line is drawn at 0.95.

The confidence level provides an estimate of how likely a result indicating two samples have different concentrations could be a false positive. The power provides an estimate of how likely false negatives are. For this the procedures for the previous set of simulations were used. For a given percentage difference between the reference and test concentrations the fraction of results which are too close together to satisfy a required confidence level is calculated. This is the fraction of results ($\beta$) which would yield false negatives for the particular concentration difference and required confidence level (in this case 95%) and the statistical power is (1-$\beta$). The results for this test are in FIGS. 6-7. The different figures are the resulting power for 2 different distributions of droplet diameters and include both the $E_1$ and $E_2$ measurement errors. FIGS. 6 and 7 are the results for uniform distributions with diameter ranges of 4 to 190 microns (FIG. 6, volume range$\approx 10^5$), and 10 to 100 microns (FIG. 7, volume range$\approx 10^3$). Each concentration on the abscissa is tested against concentrations which are 20% and 50% larger (1.2 fold and 1.5 fold resolution, respectively). The results in all of the figures are for sets of 5000 droplets and the other parameters are the same as used in the pairs method for estimating the confidence.

When distinguishing between samples whose concentrations differ by 20% this method is capable of powers >0.95 for a range of concentrations which span a factor of $\approx$100. If the requirement is relaxed from 1.2 fold to 1.5 fold resolution, the range of concentrations for which the power is >0.95 is spans more than a factor of $10^4$ for the broad uniform distribution (FIG. 6, droplet diameters ranging from 4 to 190 microns) and almost $10^4$ for the other one (FIG. 7, droplet diameters ranging from 10 to 100 microns). The location of that range depends on the shape of the droplet size distribution. The range for which the power is >0.95 increases if the required resolution is relaxed or the number of droplets is increased.

The total volume of sample in a 5,000 droplet sample for the uniform distribution ranging from 4 to 190 microns is approximately 5 uL. The total number of copies in the 8×10$^{-9}$ simulation is approximately 35/5000 droplets, or about 7800 copies/ml. Smaller concentrations can be reached using a range of droplets which include larger sized droplets or larger numbers of droplets.

Example 2

Experimental Method for the Generation of Droplets with Variable Volume and Determining their Size Droplets of variable size can be created in various ways. In one method microfluidics can be used to generate droplets of various sizes at a T-junction or flow-focusing device. This uses specialized chips into which the two components (oil phase and aqueous sample) have to be loaded first, before the aqueous sample becomes digitized by droplet formation. In this example, we employed a simpler, more user-friendly method in which droplets of various sizes are generated randomly, namely by emulsification in a test tube or otherwise suitable container. In the first embodiment, the aqueous phase containing the reaction mix is pipetted into a 0.2 mL PCR test tube that is prefilled with an appropriate oil-surfactant mix. As provided herein, the oil phase consisted of 73% Tegosoft®, 20% light mineral oil and 7% ABIL WE 09 surfactant, which were freshly mixed and equilibrated for at least 30 minutes before use. Emulsions formed with this mixture tend to show superior thermostability during standard emulsion PCR. After pipetting the aqueous phase to the oil mix, droplets of variable size were formed by vortexing for about ten seconds at about 3000 rpm. Emulsification can be further enhanced by adding a small stir bar to the mix, which during the vortexing promotes breakup of the aqueous phase into smaller droplets. The presence of the surfactant in the oil stabilizes the emulsion, such that the individual aqueous droplets did not fuse. In another embodiment, aqueous phase and oil mix were added to a small collection microtube, containing a small stainless steel bead. The tube was subsequently shaken at 15-17 Hz for 20 seconds to generate the emulsion. The emulsion was then transferred into a 0.2 mL PCR test tube for running the PCR reaction.

Figure 8A:
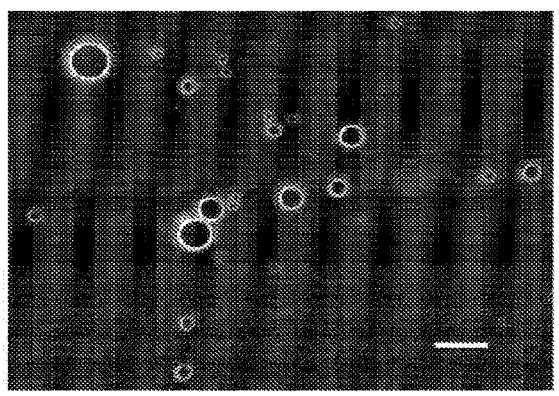
FIGS. 8A-8B depict the determination of the size of emulsified droplets using microscopy, in accordance with an example embodiment of the present invention.

In order to measure the distribution of droplet sizes, a small volume of the emulsion was spread out on a silanized glass slide and covered with an excess volume of the oil-surfactant mix. The sample was then placed under a widefield microscope and illuminated from the bottom with dark field illumination. In this scheme, an opaque disc of suitable dimension is placed in the light path of the illumination source, blocking out most of the light before the specimen. As a result only light from an outer ring of illumination reaches the specimen. The position of the opaque disc is matched to the microscope objective such, that only a small portion of light that is scattered from the specimen can enter the objective lens. Since the sample contrast comes from light that is scattered from the sample, the resulting image is dominated by the ring shaped circumference of the individual droplets as shown in FIG. 8A. Due to the large contrast obtained in dark field, the droplet diameter can be easily determined for each circle in the image, provided the droplets are sparsely enough distributed.

Figure 8B:
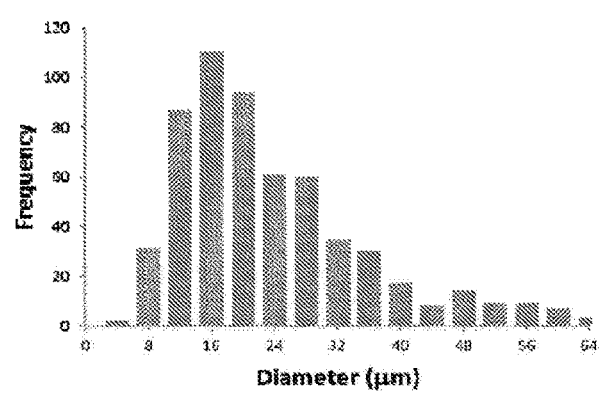

FIG. 8B shows the distribution of 577 droplets after emulsification. The distribution is highly asymmetric with a median diameter of 20 μm. This emulsification preferentially generated smaller droplets around 10-40 μm, where the smallest droplets had a diameter of about 6-8 μm, and the largest droplet diameter found was of the order of 70-80 μm. This factor of 10 in droplet diameter translates into a dynamic volume range of roughly 1000.

Figure 9:
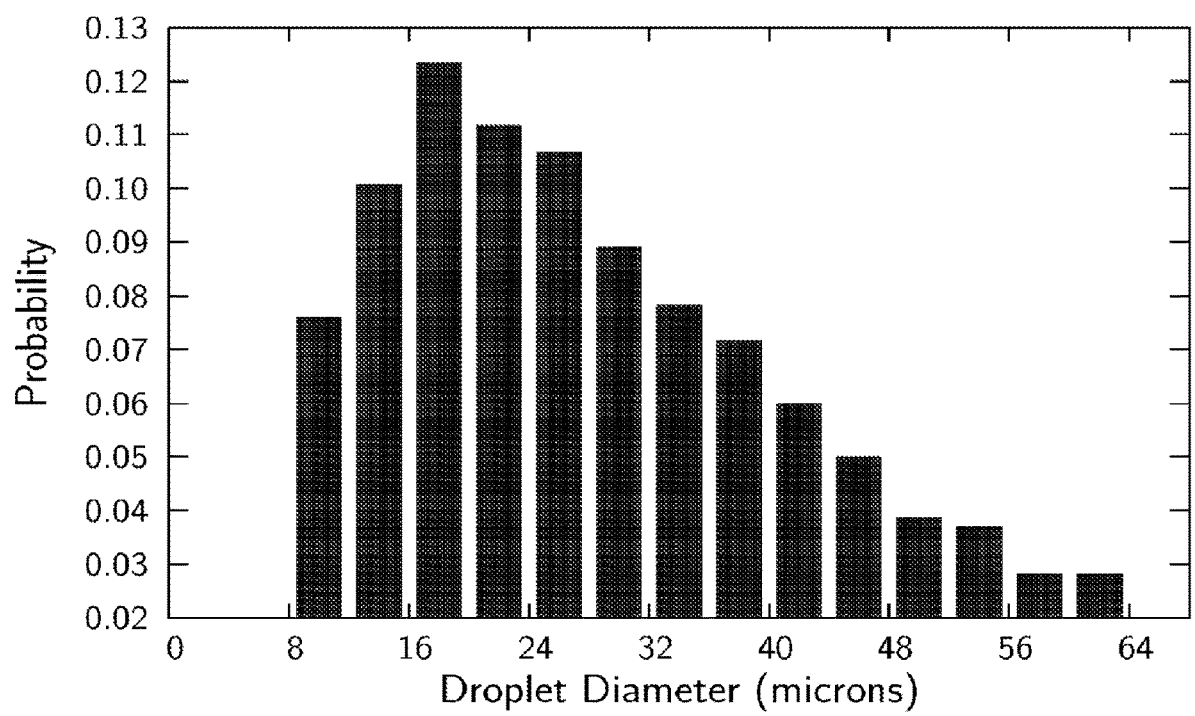
FIG. 9 shows a clipped lognormal distribution used for simulations in Table 3 of the specification. The distribution is an idealized approximation to the experimental distribution shown in FIG. 8B.

As demonstrated in FIG. 8B any real process used to generate the varying sizes of droplets is more likely to produce a peaked rather than a uniform distribution. To verify, that our conclusions derived from a uniform distribution of droplet sizes remain valid for a peaked distribution like that obtained in the experiment, we simulated digital PCR experiments with droplets, whose size distribution is shown in FIG. 9. The distribution is a lognormal distribution in which only diameters between 8 and 64 microns are included. This distribution was used in the same type of simulations performed for Table 1, and the results are listed in Table 3.

TABLE 3

Effects of volume measurement errors in simulations of 2000 droplets with non uniform distribution

| Simulation | Best fit using V | | Best fit using $\hat{V}$ | |
|---|---|---|---|---|
| $C_S$ | C | $\sigma_C$ | C | $\sigma_C$ |
| $E_1$ (±1.0 micron or 8% error(a)) | | | | |
| $2.00 \times 10^{-7}$ | $2.01 \times 10^{-7}$ | $6.14 \times 10^{-8}$ | $1.97 \times 10^{-7}$ | $6.03 \times 10^{-8}$ |
| $2.00 \times 10^{-6}$ | $2.01 \times 10^{-6}$ | $2.13 \times 10^{-7}$ | $1.97 \times 10^{-6}$ | $2.11 \times 10^{-7}$ |
| $2.00 \times 10^{-5}$ | $2.00 \times 10^{-5}$ | $8.89 \times 10^{-7}$ | $2.01 \times 10^{-5}$ | $9.11 \times 10^{-7}$ |
| $2.00 \times 10^{-4}$ | $2.00 \times 10^{-4}$ | $8.76 \times 10^{-6}$ | $2.04 \times 10^{-4}$ | $9.10 \times 10^{-6}$ |
| $2.00 \times 10^{-3}$ | $2.01 \times 10^{-3}$ | $1.46 \times 10^{-4}$ | $2.09 \times 10^{-3}$ | $1.59 \times 10^{-4}$ |
| $E_2$ (±2.0 micron or 15% error(a)) | | | | |
| $2.00 \times 10^{-7}$ | $2.00 \times 10^{-7}$ | $6.16 \times 10^{-8}$ | $1.87 \times 10^{-7}$ | $5.79 \times 10^{-8}$ |
| $2.00 \times 10^{-6}$ | $1.99 \times 10^{-6}$ | $2.13 \times 10^{-7}$ | $1.89 \times 10^{-6}$ | $2.06 \times 10^{-7}$ |
| $2.00 \times 10^{-5}$ | $2.00 \times 10^{-5}$ | $8.76 \times 10^{-7}$ | $2.01 \times 10^{-5}$ | $9.39 \times 10^{-7}$ |
| $2.00 \times 10^{-4}$ | $2.00 \times 10^{-4}$ | $8.73 \times 10^{-6}$ | $2.13 \times 10^{-4}$ | $9.95 \times 10^{-6}$ |
| $2.00 \times 10^{-3}$ | $2.02 \times 10^{-3}$ | $1.44 \times 10^{-4}$ | $2.36 \times 10^{-3}$ | $2.00 \times 10^{-4}$ |

(a)The larger of the fixed and relative errors for each droplet is used as the standard deviation of the Gaussian distributed error added to that droplet to generated simulated measured diameters from the simulated diameters. These are used to calculate the simulated measured volumes ($\hat{V}$) and simulated volumes (V), respectively.

The results in Table 3 suggest that it even with an asymmetric distribution of modest dynamic range it is possible to obtain reasonably accurate (±10%) estimates of the analyte molecule concentrations over fairly substantial concentration ranges. This is important, since it shows that a simple process like emulsification, which can be performed in almost all laboratory settings, can produce a large enough distribution of droplets to accurately determine target DNA concentrations over 4-5 orders of magnitude. Small refinements can improve this dynamic range even further.

Figure 10:
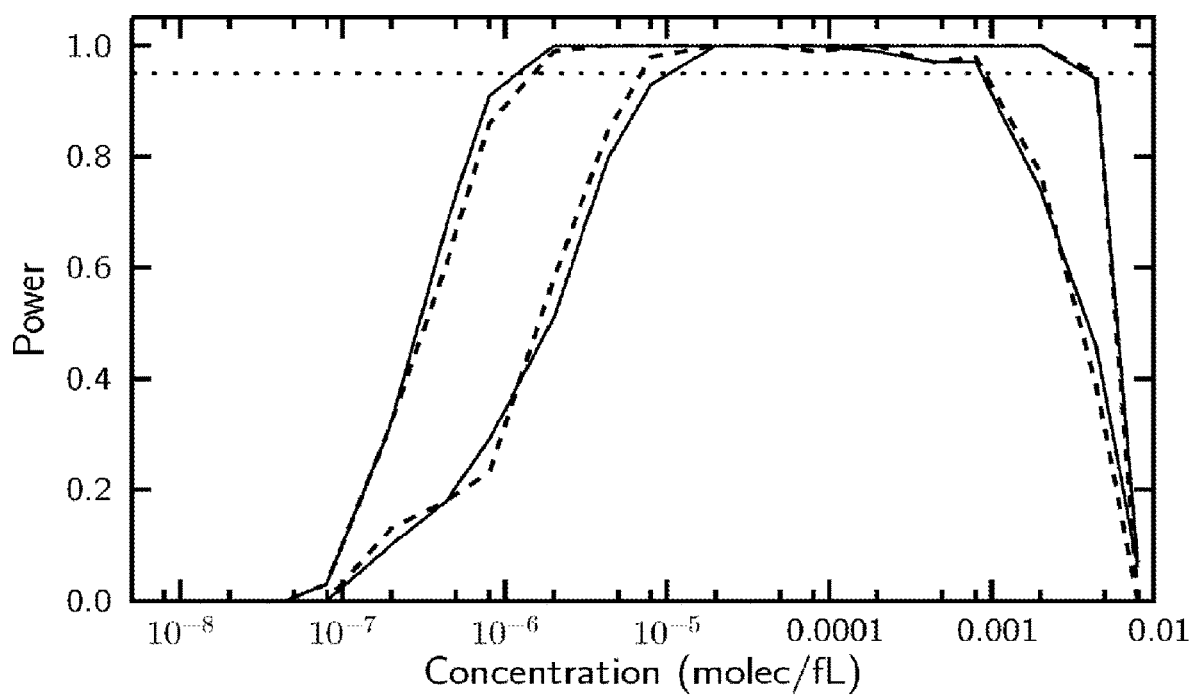
FIG. 10 depicts estimated power for clipped lognormal droplet distribution displayed in FIG. 9. The dashed lines are for measurement errors of size $E_1$ and the solid lines are for measurement errors of size $E_2$. The lower two lines are for a 1.2 fold resolution, and the upper two lines are for a 1.5 fold resolution. The dotted line is drawn at 0.95.
Figure 11A:
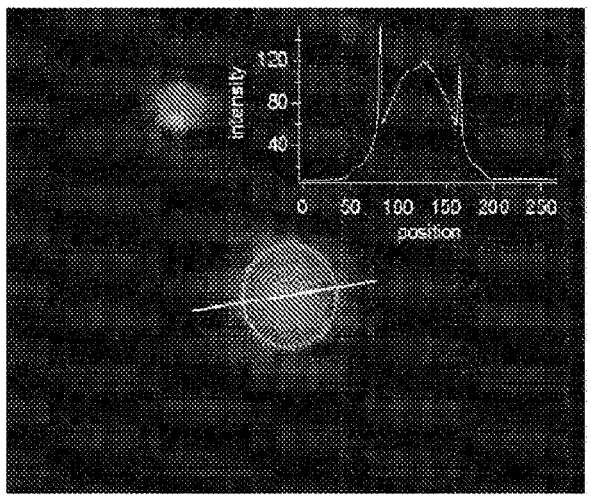
FIGS. 11A-11D show detection of PCR amplification in droplets, in accordance with an example embodiment of the present invention.
Figure 11B:
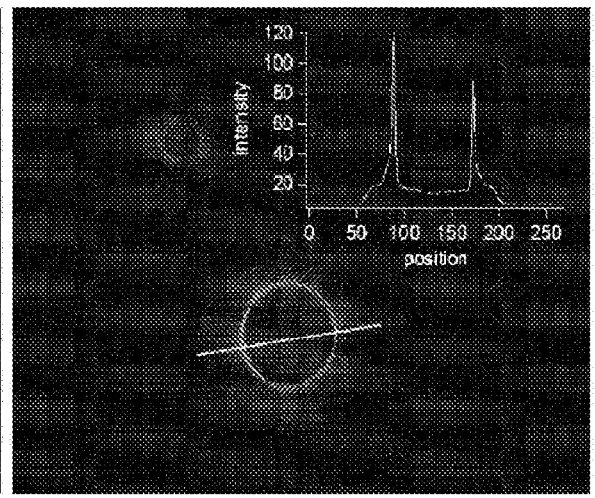
Figure 11C:
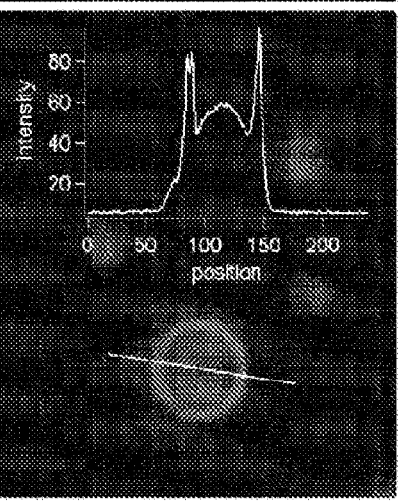
Figure 11D:
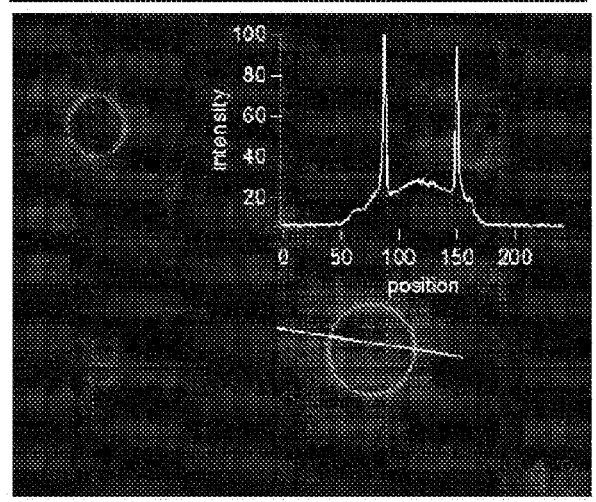

As a further test we estimated the power of the method for clipped LogNormal function that is displayed in FIG. 10 (volume range≈500). As in the case of FIGS. 6 and 7, four sets of simulations were performed spanning the concentration range from $8 \times 10^{-9}$ to $8 \times 10^{-3}$ molecules/fL. The data show that the power that can be achieved with the experimental distribution of droplets is comparable to that estimated for the case of uniformly distributed droplets of similar range (FIG. 7). The simple and user-friendly procedure of generating droplets in emulsion, combined with the robust performance of the analysis should make this invention appealing as a new method to perform digital assays with increased dynamic range.

Analysis of Amplification After dPCR

In order to visualize the presence of amplification product within a droplet, a fluorescence probe is added into the reaction mix that specifically recognizes the presence of the amplicon. In most cases this is either a molecular beacon, i.e. a hairpin structure, whose fluorescence is highly quenched in its closed conformation and whose intensity is increased once it hybridizes to amplified target DNA, or a Taqman® probe, which hybridizes to the target DNA, and leading to cleavage of a fluorescent reporter from the probe DNA during the next amplification step.

These probes have a non-negligible background fluorescence and the relative increase in intensity during amplification can be rather small, depending of the amount of probe added to the reaction. Furthermore, the excitation intensity might vary across the field of view during the detection process. A simple intensity measure can thus sometimes lead to ambiguous results, since the data usually has to be thresholded to determine whether the change in fluorescence is significant to indicate the generation of amplification product. In all our experiments we therefore add a small amount (1-2 µM) of the red fluorescent dye Rhodamine as a reference dye into the reaction mix, whose spectral signature can be well separated from the fluorescence probe that reports on amplification. We then build the ratio of two intensities, one measured from the reference dye and one measured from the probe. The intensity ratio will not be affected by changes in droplet volume due to fusion or shrinkage, or unwanted changes in the excitation power, since this would affect both dyes in the same way, but leaving their ratio unchanged. FIGS. 11A-11D show images for two PCR reactions, where (1) the droplets contained no target DNA during amplification (negative control) and (2) the reaction mix contained target DNA. Fluorescence images that show the presence of the reference dye (ROX) and probe (FAM), were taken in epifluorescence, while the droplets were simultaneously imaged in dark field through bottom illumination. The insets show the measured intensity across a line through the center of the droplets. In the absence of target DNA (A,B) the intensity in the FAM channel is dominated by the dark field signal from the droplets, with the center portion showing no increase in signal, while in the ROX channel the dark field signal superimposes on a Gaussian shaped fluorescence signal from the reference dye. The ratio between the intensity from the center region in the ROX and FAM channel is large (ROX:FAM=120:20=6:1). In the presence of DNA in the reaction mix (C,D) an increased signal in the droplet center is also observed in the FAM channel, indicating that amplification took place in that droplet. Consequently, the ratio between ROX and FAM fluorescence is significantly smaller, ROX:FAM=60:30=2:1.

One other way in which this invention could be implemented is with different groups of droplets containing the sample solution at different dilutions. The droplets containing the sample at different dilutions would have to be kept separate from each other. If that could be done, then the only change to the analysis of the experiment would be the replacement of factors of the volume in the equations by $d_i V_i$, where $d_i$ is the dilution factor for the ith droplet. For instance, equation (2) would become $$P(0, C_S d_i V_i) = \exp(-C_S d_i V_i)$$

$$P(n>0, C_S d_1 V_i) = 1 - \exp(-C_S d_i V_i) \qquad (6)$$

with similar changes for the other equations. This would permit the extension of the method to accurately measure larger concentrations than the droplet size distribution would otherwise be capable of.

Example 3

Example of Digital Isothermal DNA Amplification

This examples describes a method that does not only apply to PCR-based DNA amplification, but also is suitable for every kind of digital assay generally known in the art. The simplicity and robustness of the method makes this example particularly useful at the point-of-care and in resource-limited settings, where the availability of specialized benchtop equipment might be limited.

Automated Sample Self-Digitization with Reproducible Droplet Formation

Figure 12A:
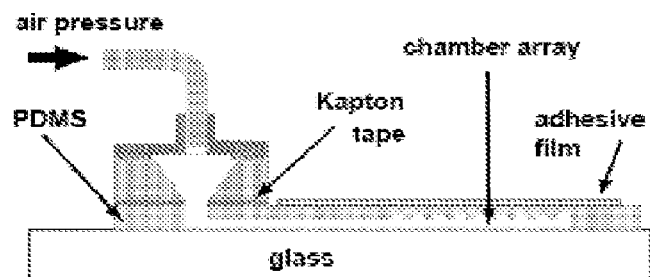
FIGS. 12A-12C depict the design of the digital LAMP self-digitization chip, in accordance with an example embodiment of the present invention.
Figure 12B:
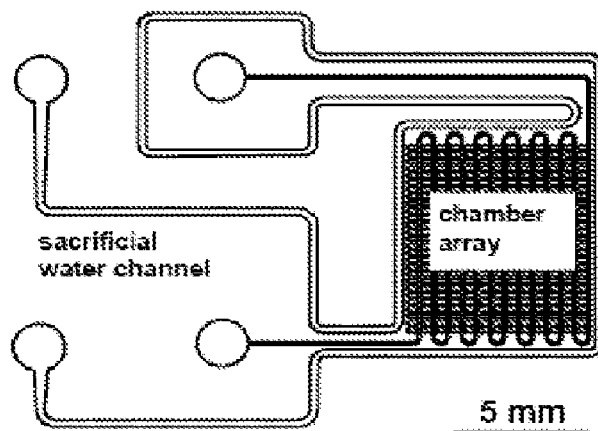
Figure 12C:
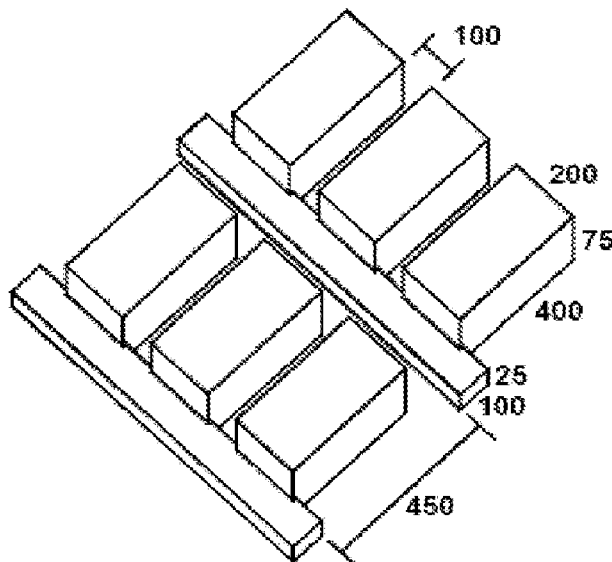

The digital LAMP chip was designed as a series of rectangular cavities to hold the droplets, which were positioned along a smaller rectangular channel used for sample delivery (FIGS. 12A-12C). The chip layout was designed to improve droplet stability and retention, automation of the filling process, and operation at elevated temperatures. A reduction of the height ratio between main channel and side cavities to ⅓ reduced the chance of crosstalk between chambers. The depth of the side chamber was extended to 400 µm, which we found to improve droplet retention. Air pressure regulated flow was used to ensure reproducibility and robustness of the automated filling. Evaporation of the aqueous droplets at higher temperatures was minimised by various measures: a) The chambers were arranged in a dense array and embedded between only a thin top and bottom layer of PDMS. b) An additional sacrificial water channel was placed around the array. c) A self-adhesive film was added on top of the chip as a vapour barrier.

Prior to loading the aqueous phase, the chip was primed with the continuous phase (light mineral oil with 0.025% w/w SPAN-80 surfactant). Fresh LAMP solution was introduced into the inlets and self-digitized into nanoliter-sized droplets inside the side chambers. FIGS. 13A and 13B show a sequence of images taken during chamber filling and droplet formation. The aqueous phase entered the main channel and slowly displaced the oil from the side chambers. Once the whole sample entered the chip, the tailing oil phase sheared off the fluids at the opening of the side compartments and isolated the nanoliter droplets.

The uniformity of droplet size across the array depended on the applied air pressure as shown in FIG. 13C. The volume of the retained droplets was estimated from images taken before chip incubation as described in the experimental section. In our setup, an air pressure between 7-8 psi yielded the most uniform distribution of droplet size, where the majority of droplets showed near complete volume retention, indicated by a relative volume fraction (RVF) near unity. Only a fraction of smaller sizes was found, most of which near the outlet where initial side-chamber filling by the aqueous phase was incomplete. Higher or lower pressures caused the RVF distribution to broaden, with more droplets showing significantly reduced RVF values.

FIG. 13D shows a cumulative histogram of 5000 droplets. More than 96% of droplets occupied at least half the chamber volume, while for 56% of all droplets, the RVF exceeded 90%. On average, we found a RVF value of 0.89±0.14. Droplet uniformity was desirable, since it reduced errors in quantification due to difference in initial droplet volume. We will show in a later section that the distribution of droplet sizes did not significantly affect the outcome of our dLAMP analysis.

FIG. 13E displays the reproducibility of sample digitization with 7 psi air pressure. For 15 individual chips, the average RVF and its standard deviation were calculated. The average RVF varied within a 10% window, which demonstrates adequate reproducibility in chip performance. Also the standard deviation in droplet size was comparable for all chips, albeit with a somewhat larger chip-to-chip variation.

Droplet Stability at Elevated Temperatures

After filling, the chip was incubated at 65° C. for 70 minutes to carry out isothermal DNA amplification. At elevated temperatures, nanoliter-sized compartments are prone to water evaporation through the PDMS and partitioning of water into the oil phase. This would result in increases in reagent concentration, for example the ionic strength, which might cause inhibition of the reaction.

Figure 14A:
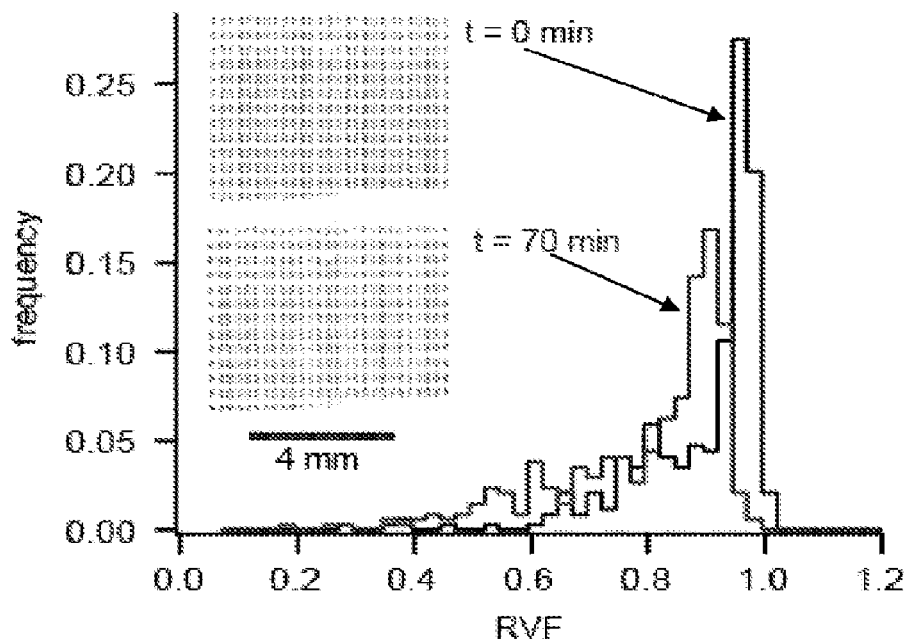
FIGS. 14A and 14B depict chip performance at elevated temperatures, in accordance with an example embodiment of the present invention.

We found the amount of sample evaporation during thermal incubation was limited to roughly 10% of the digitized volume (FIG. 14A). Chambers located at the periphery of the chip were exposed to more bulk PDMS and showed a slightly higher shrinkage as compared to chambers located in the center of the array (see inlet images of FIG. 14A). The overall effect, however, was small and we did not expect it to affect the amplification reaction. If the peripheral evaporation is still a concern, the respective chambers could be ignored and only the innermost chambers could be considered for further analysis, as will be discussed below.

Figure 14B:
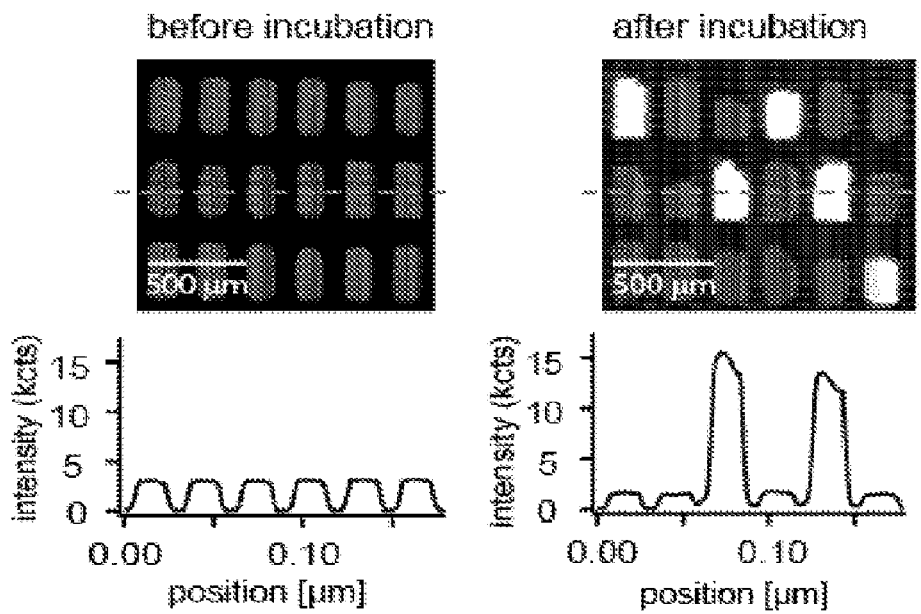

During incubation at 65° C., we expect isothermal DNA amplification to proceed in those compartments that contained one or more DNA templates. Positive amplification was evidenced by a large increase in Calcein fluorescence after pyrophosphate is released during the amplification process. Those compartments that contained no template DNA should only show background fluorescence. We next tested whether we could obtain a digital signature by amplification of a diluted sample of DNA (430-fold dilution of the stock solution). FIG. 14B shows images and intensity scans across a section of a chip before and after incubation. As expected, some chambers showed a significant increase in fluorescence, while neighbouring chambers remained dark. Crosstalk between chambers thus appeared not to be an issue: LAMP-competent chambers were well separated by neighbouring chambers that showed only background signal.

Droplet Size Variation Does Not Affect dLAMP Analysis

Smaller droplets have a lower probability of containing one or more template molecules; positive events are less likely to occur in smaller droplets and should thus be weighted more in the analysis. To test whether such a procedure would differ from results obtained by straightforward counting of LAMP-active compartments, we compared these two analysis schemes for three representative chips at three different initial template concentrations $c_i$ ($c_i = c_0/150$ (A), $c_i = c_0/430$ (B) and $c_i = c_0/1300$ (C)). Table 4 summarizes the results. In the first case, the fraction of LAMP-active chambers, $f_0$, was inferred from simple counting of positive droplets, regardless of initial droplet size. This was compared to an "effective" fraction, $f_{eff}$, which we approximated based on the initial droplet volume. $f_{eff}$ was calculated as the sum of the inverse relative volume fractions for all positive droplets. In other words, a droplet that had a RVF of 50%, contributed twice as much as a droplet that occupied the full side chamber. We then compared the ratios of $f_0$ and $f_{eff}$ between the three chips that were analysed. We found that for our system, both analysis schemes gave similar results in all parameters. The roughly 10% increase of $f_{eff}$ over $f_0$ reflects the 10-15% variation in initial droplet size. From this comparison, we concluded that in our experiments the homogeneity of initial droplet size was good enough to validate the straightforward counting method.

TABLE 4

Comparison of dLAMP analysis schemes

| | $f_0$ (all droplets) | $f_{eff}$ (all droplets) | $F_{inner}$ (inner droplets) |
|---|---|---|---|
| $c_i = c_0/150$ (A) | 0.309 | 0.338 | 0.292 |
| $c_i = c_0/430$ (B) | 0.092 | 0.104 | 0.092 |
| $c_i = c_0/1300$ (C) | 0.034 | 0.040 | 0.035 |
| $f_X^A/f_X^B$ | 3.4 | 3.3 | 3.2 |
| $f_X^A/f_X^C$ | 9.0 | 8.5 | 8.3 |
| $f_X^B/f_X^C$ | 2.7 | 2.6 | 2.6 |

We also checked whether the preferential shrinkage of the peripheral droplets affected the analysis. We compared the fraction of LAMP-competent chambers for the case when: a) all droplets are considered in the analysis ($f_0$), and b) the peripheral droplets were excluded from the analysis ($f_{inner}$). Recall that the increased shrinkage might increase local solute concentrations, which could affect the amplification process. For all three concentrations considered, the relative fraction of LAMP-competent droplets did change by less than 6%, if only the innermost droplets were analysed. The respective ratios for the different sample concentrations agreed to within 10% of each other. For dLAMP, we therefore considered all droplets in the analysis, thus avoiding unnecessary sample waste due to exclusion of the peripheral droplets.

dLAMP Quantifies Relative and Absolute DNA Concentrations

An important application of digital DNA amplification is the quantification of absolute template concentration in a sample. We next analysed the performance of the dLAMP chip with a serial dilution of DNA template in the sample. If on average less than one template is confined in the droplet, then we expect the number of LAMP-competent chambers to scale approximately linearly with DNA concentration. The template consisted of the DNA control sample provided with the LoopAmp® kit. We first performed UV absorption spectroscopy to estimate the template concentration in the DNA stock solution. The amount of DNA was too small to provide a quantifiable absorption at 260 nm. We therefore attempted DNA quantification using an intercalating dye. In this experiment, the target template was compared to a dilution series of λ-phage DNA of known concentration. All samples were incubated with a DNA intercalating dye (Evagreen®, Biotium, Hayward, Calif., USA) for 30 minutes. The fluorescence signal of each sample was then quantified on the Typhoon™ imager. Since concentration and length of the λ-phage DNA were known (48502 bp), we obtained at least an accurate estimate of the number of bp present in the template solution. The intensity from the unknown sample was comparable to the intensity from solutions of less than $10^5$ λ-phage DNA per Because of the low contrast in this concentration regime, we could not narrow down the concentration further. Assuming the plasmid being comparable in size to a full λ-phage DNA, we thus estimate a concentration between $10^4$ and $10^5$ template copies per μl.

To determine the concentration from dLAMP experiments, we first performed dLAMP on a dilution series of template concentrations ranging from 1/4 to 1/1300 of the stock solution. Each experiment was done at least in triplicate. FIGS. 15A-15F show representative images of several chips after 70 minutes incubation at 65° C. FIG. 16A shows the respective fraction of LAMP-competent chambers, $f_0$. To calculate $f_0$, we first determined the number of initial chambers before incubation, $n_i$. We then counted the number of amplified chambers, $n_a$, which were chambers that had at least a three-fold increase in fluorescence over background as quantified from the image taken after incubation. $f_0$ was then calculated as $f_0=n_a/n_i$.

We observed a linear change in the number of LAMP-competent chambers with DNA concentration for the 3 lowest concentrations analysed. To estimate the concentration of target DNA via dLAMP, we computed a linearized Poisson fit to the three lowest sample concentrations. The fit yielded a concentration of $(0.99\pm0.03)\times10^4$ copies per µl, which is in good agreement with our estimate from the DNA intercalation experiment. This result confirmed that our dLAMP chip was able to accurately reproduce relative changes in DNA concentration in a serial dilution of an unknown sample. Given the inaccuracy in the determination of the original DNA concentration, however, the data did not necessarily demonstrate our ability to determine absolute DNA concentrations with dLAMP. We therefore performed additional dLAMP experiments with a new target template of known concentration.

We chose the full λ-phage DNA template used for the intercalation assay with a set of corresponding LAMP primers. The DNA concentration in the stock solution was measured via UV spectrophotometry to be 465 µg/ml, which corresponded to $8.9\times10^9$ copies per µl. The sample was then diluted down to 20 copies per µl in the final LAMP solution. For this concentration and a side chamber volume of 6 nanoliter, we expected to observe amplification in about 12% of all chambers to occur. dLAMP was performed for 70 minutes and FIG. 16B shows images of a 535 well chip before and after the LAMP reaction. From the initial number of droplets discretized on-chip (479) and the number of LAMP-competent chambers after incubation (47) we computed a relative fraction of 9.8% of positive events. A second experiment in a 351 chamber array yielded a comparable fraction of 10.7% for the same template concentration. The small difference between expected and measured values for $f_a$ can probably be attributed to pipetting errors accumulating over the 8-fold dilution series.

We therefore concluded that our dLAMP chip was capable of correctly determining absolute DNA concentrations as well as relative changes in DNA concentrations. Together with its simple operation, dLAMP in a SD chip provides a convenient platform to perform isothermal, digital DNA quantification with minimum sample consumption.

We demonstrated successful on-chip loop-mediated DNA amplification in a digital format. Driven by the limits of existing platforms to perform digital DNA amplification in a simple-to-use format with minimum sample consumption, we refined our self-digitization concept to allow for isothermal DNA amplification at 65° C. Our method is simple and robust: once the aqueous phase is pipetted into the chip, the use of a simple pump head and constant air pressure is sufficient to induce sample discretization without the need of further chip manipulation, such as pneumatic valving or mechanical action. Unlike most (if not all) other reported digitization platforms, our design offers complete loss-less sample compartmentalization. This is important in cases where sample availability is limited, such as point-of-care applications.

Digital LAMP signatures reproduced absolute DNA concentrations as well as relative changes with sufficient accuracy within an incubation period of 70 minutes. Droplet shrinkage during sample incubation at elevated temperatures was minimal and did not affect the amplification process. We also addressed the issue of variations in droplet size during chip filling and demonstrated sufficient size homogeneity, with droplet volumes varying around 10-15%. Differences in droplet volume can potentially affect the average number of templates per droplet and the resulting digital signature. We verified that our autonomous chip filling produced droplets with sufficiently homogeneous volumes so that data analysis simplifies to the counting of LAMP-competent chambers, without the need to consider the variation in droplet volume.

Our experimental protocol utilizes standard lab instrumentation for heating and imaging and as such is compatible with most diagnostic settings, as no additional custom-built instrumentation is required. Because of the moderate reaction temperature of 65° C., chip incubation could also be done in a thermal water bath, which would further simplify chip operation. Finally we note that, besides the increase in Calcein fluorescence, LAMP potentially generates a visual signal from precipitation of the pyrophosphate. Detection could be performed on a simple microscope, which would ultimately obviate the need for fluorescence equipment and reduce assay complexity even further.

Experimental Section on dLAMP

Chemicals and Reagents

The LoopAmp® DNA amplification kit and the Calcein fluorescence indicator kit were purchased from SA Scientific (San Antonio, Tex., USA). Positive control DNA and with a set of corresponding primers was included in the kit. Light mineral oil, sorbitan monooleate (SPAN-80), bovine serum albumin (BSA), propylene glycol methyl ether acetate (PGMEA) and isopropyl alcohol were obtained from Sigma Aldrich (St. Louis, Mo., USA). Polydimethylsiloxane (PDMS, Sylgard 184 kit) was purchased from Dow Corning (Midland, Mich., USA).

For the LAMP experiments on the full λ-phage DNA, the following set of 6 primers was used (forward inner primer (FIP): 5'-CAGCATCCCTTTCGGCATACCAGGTG-GCAAGGGTAATGAGG-3' (SEQ ID NO:1), backward inner primer (BIP): 5'-GGAGGTTGAAGAACTGCGGCA-GTCGATGGCGTTCGTACTC-3' (SEQ ID NO:2), forward outer primer (F3): 5'-GAATGCCCGTTCTGCGAG-3' (SEQ ID NO:3), backward outer primer (B3): 5'-TTCAGTTCCT-GTGCGTCG-3' (SEQ ID NO:4), loop forward primer (LF), 5'-GGCGGCAGAGTCATAAAGCA-3' (SEQ ID NO:5), and loop backward primer (LB): 5'-GGCAGATCTCCAGC-CAGGAACTA-3' (SEQ ID NO:6). All primers were purchased from IDT (San Diego, Calif., USA).

Microfluidic Chip Fabrication

Microfluidic chips for digital LAMP were replicated in polydimethylsiloxane (PDMS) with standard soft lithography. The network of microfluidic channels and side chambers was designed in AutoCAD (Autodesk, San Rafael, Calif., USA) and printed onto a Mylar photomask (Fineline Imaging, Colorado Springs Colo., USA). The mask was used to fabricate a two layer SU-8 on-silicon master. For each layer, the following steps were performed: SU-8 photoresist (SU-8 2050, MicroChem, Newton, Mass., USA) was spin coated onto a freshly cleaned silicon wafer. After soft baking, wafer and photomask were aligned and exposed to UV in a commercial mask aligner (Newport, Irvine Calif., USA). UV exposure led to crosslinking of SU-8 underneath the transparent areas of the photomask. After curing, non-exposed SU-8 was dissolved in PGMEA and the wafer was cleaned with isopropyl alcohol and hard baked for 10 minutes at 155° C. The height of the positive features in the master was measured in a home-built interferometer to be around 75 µm. To avoid sticking of PDMS onto the wafer during replication, the wafer was coated with (tridecafluoro)-1,1,2,2-tetrahydrooctyl) trichlorosilane (Gelest, Morrisville, Pa., USA) by gas-phase deposition.

For chip replication, PDMS base and catalyst were mixed in a 10:1 weight ratio as recommended by the manufacturer. The mix was degassed for 15-20 minutes and spin coated onto the SU-8 on-silicon master to form a thin film, approximately 300 μm thick. After curing at 70° C. for 3 hours, the PDMS was peeled off the wafer. Access holes were punched into the elastomer with a sharpened 15 gauge punch. The PDMS replica was bonded to a microscope slide coated with a thin layer of cured PDMS via oxygen plasma treatment. The PDMS chip was stored at 115° C. for 2 days, which reverted the surface back to hydrophobic.

Experimental Protocol

Prior to the experiment, a set of small troughs matching the inlet and outlet holes was replicated into PDMS and attached to the chip with double-sided tape. Each trough provided a reservoir of approximately 50 μl. The chip was placed under vacuum for 20-30 minutes to remove excess air from the bulk PDMS. 40 μl of light mineral oil supplemented with 0.025% w/w SPAN-80 were placed into the inlet of the main channel to prime the chip. Air pressure was applied to maintain oil flow until the air was driven out of the chip. After priming, the chip was covered with a small piece of adhesive PCR sealant film (Bio-Rad, Hercules, Calif., USA) to reduce water evaporation during the incubation.

13 μl of LAMP solution were freshly prepared following the manufacturer's protocol. The mix was supplemented with 1.2 g/l BSA to stabilise the polymerase during the reaction and 0.6 μl of the Calcein-based fluorescence detection kit. 1.8-2 μl of LAMP solution were pipetted into the inlet and formed an aqueous plug at the bottom of the trough that was covered with excess oil. External air pressure was applied to move the aqueous plug through the channel network until the whole sample became digitized on-chip. Digitization was visually checked on a microscope (AZ 100, Nikon Instruments, Melville N.Y., USA). The sacrificial water channel was manually filled with degased water using negative pressure on the outlet. All inlets were covered with at least 20 μl of oil before the chip was incubated at 65° C. for 70 minutes on a Thermocycler fitted with in situ adaptor (Mastercycler, Eppendorf, Westbury, N.Y., USA).

Chip Imaging and Quantification

Before and after thermal incubation, all chips were scanned on a variable mode imager (Typhoon FLA9000, GE Healthcare, Pittsburgh, Pa., USA). The Calcein fluorescence inside the chambers was excited at 473 nm and images were taken through a long pass filter (510LP) with 10 μm pixel resolution and a voltage of 350V applied to the photomultiplier tube. Subsequent image analysis was performed in ImageJ (rsbweb.nih.gov) to quantify the number and size distribution of discretized volumes as well as the number of chambers that showed DNA amplification. Further data analysis was done with IGOR Pro (WaveMetrics, Lake Oswego, Oreg., USA). Although initially the Calcein fluorescence was highly quenched, its residual emission could still be monitored with the Typhoon imager to determine initial droplet size in the chamber. The distribution of initial droplet sizes was quantified in terms of the retained volume fraction (RVF) estimated as the ratio of the droplet area to the area of the side chamber. A threshold equal to ⅓ of the average pixel intensity of the Calcein fluorescence in droplets was used to discriminate against background. Only droplets with a RVF of at least 0.15 were considered for further analysis.

As provided herein, a statistical analysis of a digital droplet assay using droplets from a continuous distribution of sizes is presented. The best fit concentrations are moderately insensitive to modest unbiased errors in the determination of the individual droplet volumes, so the required accuracy of that determination should not be an unreasonable burden. A simple method for estimating the confidence when comparing results from different samples is presented. It produces estimates of the confidence in reasonable agreement with a more computationally intensive estimate of the confidence. From simulations, the statistical power of the method can be calculated for three different distributions of the droplet diameters for 1.2 and 1.5 fold resolutions. Given a desired resolution, droplet size distribution and number of droplets, these methods can be used to determine the range of concentrations for which this method should yield usable results.

While the present invention has been described with an emphasis on certain embodiments, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being defined by the following claims.

What is claimed is:

1. A method for using digital measurements to determine a concentration of an analyte in a sample, the method comprising:
   producing a plurality of droplets, wherein at least one of the droplets of the plurality of droplets comprises the analyte from the sample and a detectable agent;
   measuring some or all of the droplets of the plurality of droplets to determine a volume of the some or all of the droplets of the plurality of droplets;
   analyzing at least a portion of the plurality of droplets to determine a number of droplets in the at least a portion of the plurality of droplets that contain the analyte and the detectable agent; and
   using the volume of the some or all of the plurality of droplets and the number of droplets in the at least a portion of the plurality of droplets that contain the analyte and the detectable agent to determine the concentration of the analyte in the sample.

2. The method of claim 1, wherein each of the plurality of droplets has an individual volume, and wherein the plurality of droplets has a volume distribution.

3. The method of claim 2, wherein the individual volumes of the plurality of droplets in the volume distribution can range by more than a factor of 2.

4. The method of claim 2, wherein the volume distribution has a volume range from about 100 nanoliters to about 1 femtoliter.

5. The method of claim 1, wherein the at least a portion of the plurality of droplets analyzed comprises the some or all of the droplets of the plurality of droplets measured.

6. The method of claim 1, wherein the plurality of droplets is produced in an emulsion by combining immiscible fluids.

7. The method of claim 6, wherein the immiscible fluids comprise water and oil.

8. The method of claim 6, wherein the emulsion comprises a surfactant.

9. The method of claim 1, wherein the analyte is a nucleic acid molecule, a peptide, a protein, or a combination thereof.

10. The method of claim 1, wherein the detectable agent is fluorescent.

11. The method of claim 1, the method further comprising conducting polymerase chain reaction, rolling circle amplification, nucleic acid sequence based amplification, loop-mediated amplification, or a combination thereof.

12. The method of claim 1, wherein the concentration of the analyte is determined over a dynamic range of at least three orders of magnitude.

13. The method of claim 1, further comprising conducting isothermal amplification.

14. A system for using digital measurements to determine a concentration of an analyte in a sample, the system comprising:
- a sample holder containing a plurality of droplets;
- a detector for detecting a detectable agent contained in at least one droplet of the plurality of droplets, the at least one droplet additionally comprising the analyte; and
- a computer comprising a memory device with executable instructions stored thereon, the instructions, when executed by a processor, cause the processor to:
  - measure some or all of the droplets of the plurality of droplets to determine a volume of the some or all of the droplets of the plurality of droplets;
  - analyze at least a portion of the plurality of droplets to determine a number of droplets in the at least a portion of the plurality of droplets that contain the analyte and the detectable agent; and
  - use the volume of the some or all of the plurality of droplets and the number of droplets in the at least a portion of the plurality of droplets that contain the analyte and the detectable agent to determine the concentration of the analyte in the sample.

15. The system of claim 14, wherein each of the plurality of droplets has an individual volume, and wherein the plurality of droplets has a volume distribution.

16. The system of claim 15, wherein the individual volumes of the plurality of droplets in the volume distribution can range by more than a factor of 2.

17. The system of claim 15, wherein the volume distribution has a volume range from about 100 nanoliters to about 1 femtoliter.

18. The system of claim 14, wherein the at least a portion of the plurality of droplets analyzed comprises the some or all of the droplets of the plurality of droplets measured.

19. The system of claim 14, wherein the plurality of droplets is produced in an emulsion by combining immiscible fluids.

20. The system of claim 19, wherein the immiscible fluids comprise water and oil.

21. The system of claim 14, wherein the detectable agent is fluorescent.

22. The system of claim 14, wherein the analyte is a nucleic acid molecule, a peptide, a protein, or a combination thereof.

23. The system of claim 14, wherein at least one of the droplets in the plurality of droplets comprises an amplified product from a polymerase chain reaction, rolling circle amplification, nucleic acid sequence based amplification, loop-mediated amplification, or a combination thereof.

24. The system of claim 14, wherein the concentration of the analyte is determined over a dynamic range of at least three orders of magnitude.

25. The system of claim 14, wherein at least one of the droplets in the plurality of droplets comprises an amplified product from an isothermal amplification.

26. The system of claim 14, wherein the sample holder is an array of wells.

27. The system of claim 14, wherein the sample holder is a microfluidic chip.

* * * * *

SEQUENCE LISTING

<160> NUMBER OF SEQ ID NOS: 6

<210> SEQ ID NO 1
<211> LENGTH: 41
<212> TYPE: DNA
<213> ORGANISM: Artificial Sequence
<220> FEATURE:
<223> OTHER INFORMATION: Synthetic: forward inner primer (FIP)

<400> SEQUENCE: 1
cagcatccct tcggcatac caggtggcaa gggtaatgag g    41

<210> SEQ ID NO 2
<211> LENGTH: 40
<212> TYPE: DNA
<213> ORGANISM: Artificial Sequence

```
<220> FEATURE:
<223> OTHER INFORMATION: Synthetic: backward inner primer (B1P)

<400> SEQUENCE: 2
ggaggttgaa gaactgcggc agtcgatggc gttcgtactc                            40

<210> SEQ ID NO 3
<211> LENGTH: 18
<212> TYPE: DNA
<213> ORGANISM: Artificial Sequence
<220> FEATURE:
<223> OTHER INFORMATION: Synthetic: forward outer primer (F3)

<400> SEQUENCE: 3
gaatgcccgt tctgcgag                                                   18

<210> SEQ ID NO 4
<211> LENGTH: 18
<212> TYPE: DNA
<213> ORGANISM: Artificial Sequence
<220> FEATURE:
<223> OTHER INFORMATION: Synthetic: backward outer primer (B3)

<400> SEQUENCE: 4
ttcagttcct gtgcgtcg                                                   18

<210> SEQ ID NO 5
<211> LENGTH: 20
<212> TYPE: DNA
<213> ORGANISM: Artificial Sequence
<220> FEATURE:
<223> OTHER INFORMATION: Synthetic: loop forward primer (LF)

<400> SEQUENCE: 5
ggcggcagag tcataaagca                                                 20

<210> SEQ ID NO 6
<211> LENGTH: 23
<212> TYPE: DNA
<213> ORGANISM: Artificial Sequence
<220> FEATURE:
<223> OTHER INFORMATION: Synthetic: loop backward primer (LB)

<400> SEQUENCE: 6
ggcagatctc cagccaggaa cta                                             23
```